(12) United States Patent
Araki et al.

(10) Patent No.: US 6,743,616 B2
(45) Date of Patent: Jun. 1, 2004

(54) HIGHLY PRODUCTIVE ALPHA-AMYLASES

(75) Inventors: Hiroyuki Araki, Haga-gun (JP); Keiji Endo, Haga-gun (JP); Hiroshi Hagihara, Haga-gun (JP); Kazuaki Igarashi, Haga-gun (JP); Yasuhiro Hayashi, Haga-gun (JP); Katsuya Ozaki, Haga-gun (JP)

(73) Assignee: Kao Corporation, Tokyo (JP)

( * ) Notice: Subject to any disclaimer, the term of this patent is extended or adjusted under 35 U.S.C. 154(b) by 15 days.

(21) Appl. No.: 09/971,611

(22) Filed: Oct. 9, 2001

(65) Prior Publication Data

US 2002/0123124 A1 Sep. 5, 2002

(30) Foreign Application Priority Data

Oct. 11, 2000 (JP) ........................................ 2000-310605

(51) Int. Cl.[7] .............................. C12N 9/00; C12N 9/28; C07H 21/04; C11D 3/00; C11D 7/42
(52) U.S. Cl. ............................... 435/202; 435/4; 435/6; 435/69.1; 435/183; 435/200; 536/23.2; 536/23.7; 510/114; 510/392; 510/515
(58) Field of Search ................................. 435/183, 200, 435/201, 202, 203, 204, 205; 536/23.2

(56) References Cited

U.S. PATENT DOCUMENTS

| | | | |
|---|---|---|---|
| 5,635,468 A | 6/1997 | Ara et al. | |
| 5,989,169 A | 11/1999 | Svendsen et al. | |
| 6,309,871 B1 * | 10/2001 | Outtrup et al. | 435/202 |
| 6,410,295 B1 * | 6/2002 | Andersen et al. | 435/202 |
| 6,436,888 B1 * | 8/2002 | Svendsen et al. | 510/226 |

FOREIGN PATENT DOCUMENTS

| | | |
|---|---|---|
| EP | 1 065 277 | 1/2001 |
| JP | 98362487 | 12/1998 |
| JP | 98362488 | 12/1998 |
| JP | 2000-184882 | 7/2000 |
| JP | 2000-184883 | 7/2000 |
| JP | 2001-54392 | 2/2001 |
| JP | 2001054392 | 2/2001 |
| WO | WO 9426881 A | 11/1994 |
| WO | WO 96/23873 | 8/1996 |
| WO | WO 98/05748 | 2/1998 |
| WO | WO 98/44126 | 10/1998 |
| WO | WO 00/60058 | 10/2000 |

OTHER PUBLICATIONS

Yuuki (a) et al. SwissProt database accession No. P06278, Jan. 1, 1988.*

Yuuki (b) et al. PIR database accession No. A91997, Jun. 30, 1987.*

A. Tsukamoto, et al., Biochemical and Biophysical Research Communications, vol. 151, No. 1, pp. 25–31, XP–000605386, "Nucleotide Sequence of the Maltohexaose–Producing Amylase Gene From an Alkalophilic Bacillus sp. #707 and Structural Similarity to Liquefying Type α–Amylases", Feb. 29, 1988.

K. Igarashi, et al., Biochemical and Biophysical Research Communications, vol. 248, No. 2, pp. 372–377, XP–002901159, "Improved Thermostability of a Bacillus α–Amylase by Deletion of an Arginine–Glycine Residue is Caused By Enhanced Calcium Binding", 1998.

* cited by examiner

Primary Examiner—Manjunath Rao
(74) Attorney, Agent, or Firm—Oblon, Spivak, McClelland, Maier & Neustadt, P.C.

(57) ABSTRACT

The invention relates to mutant α-amylases that may be produced at high yield from recombinant microorganisms.

26 Claims, 2 Drawing Sheets

SEQUENCE LISTING

<160> NUMBER OF SEQ ID NOS: 51

<210> SEQ ID NO 1
<211> LENGTH: 1786
<212> TYPE: DNA
<213> ORGANISM: Bacillus sp. KSM-AP1378
<220> FEATURE:
<221> NAME/KEY: sig_peptide
<222> LOCATION: (155)..(247)
<223> OTHER INFORMATION:
<221> NAME/KEY: mat_peptide
<222> LOCATION: (248)..()
<223> OTHER INFORMATION:
<221> NAME/KEY: CDS
<222> LOCATION: (155)..(1702)
<223> OTHER INFORMATION:

<400> SEQUENCE: 1

```
cagcgtgata atataaattt gaaatgaaca cctatgaaaa tatggtagcg attgcgcgac      60
gagaaaaaac ttgggagtta ggaagtgata ttaaaggatt tttttttgact tgttgtgaaa    120 acgcttgcat aaattgaagg agagggtgct tttt atg aaa ctt cat aac cgt ata     175
                                      Met Lys Leu His Asn Arg Ile
                                                 -30             -25 att agc gta cta tta aca cta ttg tta gct gta gct gtt ttg ttt cca       223
Ile Ser Val Leu Leu Thr Leu Leu Leu Ala Val Ala Val Leu Phe Pro
            -20                 -15                 -10 tat atg acg gaa cca gca caa gcc cat cat aat ggg acg aat ggg acc       271
Tyr Met Thr Glu Pro Ala Gln Ala His His Asn Gly Thr Asn Gly Thr
         -5             -1   1                   5 atg atg cag tat ttt gaa tgg cat ttg cca aat gac ggg aac cac tgg       319
Met Met Gln Tyr Phe Glu Trp His Leu Pro Asn Asp Gly Asn His Trp
     10                  15                  20 aac agg tta cga gat gac gca gct aac tta aag agt aaa ggg att acc       367
Asn Arg Leu Arg Asp Asp Ala Ala Asn Leu Lys Ser Lys Gly Ile Thr
 25                 30                  35                  40 gct gtt tgg att cct cct gca tgg aag ggg act tcg caa aat gat gtt       415
Ala Val Trp Ile Pro Pro Ala Trp Lys Gly Thr Ser Gln Asn Asp Val
                     45                  50                  55 ggg tat ggt gcc tat gat ttg tac gat ctt ggt gag ttt aac caa aag       463
Gly Tyr Gly Ala Tyr Asp Leu Tyr Asp Leu Gly Glu Phe Asn Gln Lys
                 60                  65                  70 gga acc gtc cgt aca aaa tat ggc aca agg agt cag ttg caa ggt gcc       511
Gly Thr Val Arg Thr Lys Tyr Gly Thr Arg Ser Gln Leu Gln Gly Ala
             75                  80                  85 gtg aca tct ttg aaa aat aac ggg att caa gtt tat ggg gat gtc gtg       559
Val Thr Ser Leu Lys Asn Asn Gly Ile Gln Val Tyr Gly Asp Val Val
         90                  95                 100
```

-continued

| | |
|---|---|
| atg aat cat aaa ggt gga gca gac ggg aca gag atg gta aat gcg gtg<br>Met Asn His Lys Gly Gly Ala Asp Gly Thr Glu Met Val Asn Ala Val<br>105                    110                    115                    120 | 607 |
| gaa gtg aac cga agc aac cga aac caa gaa ata tca ggt gaa tac acc<br>Glu Val Asn Arg Ser Asn Arg Asn Gln Glu Ile Ser Gly Glu Tyr Thr<br>                    125                    130                    135 | 655 |
| att gaa gca tgg acg aaa ttt gat ttc cct gga aga gga aat acc cat<br>Ile Glu Ala Trp Thr Lys Phe Asp Phe Pro Gly Arg Gly Asn Thr His<br>              140                    145                    150 | 703 |
| tcc aac ttt aaa tgg cgc tgg tat cat ttt gat ggg aca gat tgg gat<br>Ser Asn Phe Lys Trp Arg Trp Tyr His Phe Asp Gly Thr Asp Trp Asp<br>              155                    160                    165 | 751 |
| cag tca cgt cag ctt cag aac aaa ata tat aaa ttc aga ggt acc gga<br>Gln Ser Arg Gln Leu Gln Asn Lys Ile Tyr Lys Phe Arg Gly Thr Gly<br>170                    175                    180 | 799 |
| aag gca tgg gac tgg gaa gta gat ata gag aac ggc aac tat gat tac<br>Lys Ala Trp Asp Trp Glu Val Asp Ile Glu Asn Gly Asn Tyr Asp Tyr<br>185                    190                    195                    200 | 847 |
| ctt atg tat gca gac att gat atg gat cat cca gaa gta atc aat gaa<br>Leu Met Tyr Ala Asp Ile Asp Met Asp His Pro Glu Val Ile Asn Glu<br>                    205                    210                    215 | 895 |
| ctt aga aat tgg gga gtt tgg tat aca aat aca ctt aat cta gat gga<br>Leu Arg Asn Trp Gly Val Trp Tyr Thr Asn Thr Leu Asn Leu Asp Gly<br>              220                    225                    230 | 943 |
| ttt aga atc gat gct gtg aaa cat att aaa tac agc tat acg aga gat<br>Phe Arg Ile Asp Ala Val Lys His Ile Lys Tyr Ser Tyr Thr Arg Asp<br>                    235                    240                    245 | 991 |
| tgg cta aca cat gtg cgt aac acc aca ggt aaa cca atg ttt gca gtt<br>Trp Leu Thr His Val Arg Asn Thr Thr Gly Lys Pro Met Phe Ala Val<br>250                    255                    260 | 1039 |
| gca gaa ttt tgg aaa aat gac ctt gct gca atc gaa aac tat tta aat<br>Ala Glu Phe Trp Lys Asn Asp Leu Ala Ala Ile Glu Asn Tyr Leu Asn<br>265                    270                    275                    280 | 1087 |
| aaa aca agt tgg aat cac tcc gtg ttc gat gtt cct ctt cat tat aat<br>Lys Thr Ser Trp Asn His Ser Val Phe Asp Val Pro Leu His Tyr Asn<br>                    285                    290                    295 | 1135 |
| ttg tac aat gca tct aat agt ggt ggc tat ttt gat atg aga aat att<br>Leu Tyr Asn Ala Ser Asn Ser Gly Gly Tyr Phe Asp Met Arg Asn Ile<br>              300                    305                    310 | 1183 |
| tta aat ggt tct gtc gta caa aaa cac cct ata cat gca gtc aca ttt<br>Leu Asn Gly Ser Val Val Gln Lys His Pro Ile His Ala Val Thr Phe<br>              315                    320                    325 | 1231 |
| gtt gat aac cat gac tct cag cca gga gaa gca ttg gaa tcc ttt gtt<br>Val Asp Asn His Asp Ser Gln Pro Gly Glu Ala Leu Glu Ser Phe Val<br>330                    335                    340 | 1279 |
| caa tcg tgg ttc aaa cca ctg gca tat gca ttg att ctg aca agg gag<br>Gln Ser Trp Phe Lys Pro Leu Ala Tyr Ala Leu Ile Leu Thr Arg Glu<br>345                    350                    355                    360 | 1327 |
| caa ggt tac cct tcc gta ttt tac ggt gat tac tac ggt ata cca act<br>Gln Gly Tyr Pro Ser Val Phe Tyr Gly Asp Tyr Tyr Gly Ile Pro Thr<br>                    365                    370                    375 | 1375 |
| cat ggt gtt cct tcg atg aaa tct aaa att gat cca ctt ctg cag gca<br>His Gly Val Pro Ser Met Lys Ser Lys Ile Asp Pro Leu Leu Gln Ala<br>              380                    385                    390 | 1423 |
| cgt caa acg tat gcc tac gga acc caa cat gat tat ttt gat cat cat<br>Arg Gln Thr Tyr Ala Tyr Gly Thr Gln His Asp Tyr Phe Asp His His<br>              395                    400                    405 | 1471 |
| gat att atc ggc tgg acg aga gaa ggg gac agc tcc cac cca aat tca<br>Asp Ile Ile Gly Trp Thr Arg Glu Gly Asp Ser Ser His Pro Asn Ser<br>              410                    415                    420 | 1519 |

-continued

```
gga ctt gca act att atg tcc gat ggg cca ggg ggt aat aaa tgg atg    1567
Gly Leu Ala Thr Ile Met Ser Asp Gly Pro Gly Gly Asn Lys Trp Met
425             430                 435                 440 tat gtc ggg aaa cat aaa gct ggc caa gta tgg aga gat atc acc gga    1615
Tyr Val Gly Lys His Lys Ala Gly Gln Val Trp Arg Asp Ile Thr Gly
                445                 450                 455 aat agg tct ggt acc gtc acc att aat gca gat ggt tgg ggg aat ttc    1663
Asn Arg Ser Gly Thr Val Thr Ile Asn Ala Asp Gly Trp Gly Asn Phe
            460                 465                 470 act gta aac gga ggg gca gtt tcg gtt tgg gtg aag caa taaataagga     1712
Thr Val Asn Gly Gly Ala Val Ser Val Trp Val Lys Gln
        475                 480                 485 acaagaggcg aaaattactt tcctacatgc agagctttcc gatcactcat acacccaata  1772
taaattggaa gctt                                                    1786
```

<210> SEQ ID NO 2
<211> LENGTH: 516
<212> TYPE: PRT
<213> ORGANISM: Bacillus sp. KSM-AP1378

<400> SEQUENCE: 2

```
Met Lys Leu His Asn Arg Ile Ile Ser Val Leu Leu Thr Leu Leu Leu
    -30             -25                 -20

Ala Val Ala Val Leu Phe Pro Tyr Met Thr Glu Pro Ala Gln Ala His
-15             -10                  -5              -1   1

His Asn Gly Thr Asn Gly Thr Met Met Gln Tyr Phe Glu Trp His Leu
            5                   10                  15

Pro Asn Asp Gly Asn His Trp Asn Arg Leu Arg Asp Asp Ala Ala Asn
        20                  25                  30

Leu Lys Ser Lys Gly Ile Thr Ala Val Trp Ile Pro Pro Ala Trp Lys
    35                  40                  45

Gly Thr Ser Gln Asn Asp Val Gly Tyr Gly Ala Tyr Asp Leu Tyr Asp
50                  55                  60                  65

Leu Gly Glu Phe Asn Gln Lys Gly Thr Val Arg Thr Lys Tyr Gly Thr
                70                  75                  80

Arg Ser Gln Leu Gln Gly Ala Val Thr Ser Leu Lys Asn Asn Gly Ile
            85                  90                  95

Gln Val Tyr Gly Asp Val Val Met Asn His Lys Gly Gly Ala Asp Gly
        100                 105                 110

Thr Glu Met Val Asn Ala Val Glu Val Asn Arg Ser Asn Arg Asn Gln
    115                 120                 125

Glu Ile Ser Gly Glu Tyr Thr Ile Glu Ala Trp Thr Lys Phe Asp Phe
130                 135                 140                 145

Pro Gly Arg Gly Asn Thr His Ser Asn Phe Lys Trp Arg Trp Tyr His
                150                 155                 160

Phe Asp Gly Thr Asp Trp Asp Gln Ser Arg Gln Leu Gln Asn Lys Ile
            165                 170                 175

Tyr Lys Phe Arg Gly Thr Gly Lys Ala Trp Asp Trp Glu Val Asp Ile
        180                 185                 190

Glu Asn Gly Asn Tyr Asp Tyr Leu Met Tyr Ala Asp Ile Asp Met Asp
    195                 200                 205

His Pro Glu Val Ile Asn Glu Leu Arg Asn Trp Gly Val Trp Tyr Thr
210                 215                 220                 225

Asn Thr Leu Asn Leu Asp Gly Phe Arg Ile Asp Ala Val Lys His Ile
                230                 235                 240
```

```
Lys Tyr Ser Tyr Thr Arg Asp Trp Leu Thr His Val Arg Asn Thr Thr
            245                 250                 255

Gly Lys Pro Met Phe Ala Val Ala Glu Phe Trp Lys Asn Asp Leu Ala
            260                 265                 270

Ala Ile Glu Asn Tyr Leu Asn Lys Thr Ser Trp Asn His Ser Val Phe
            275                 280                 285

Asp Val Pro Leu His Tyr Asn Leu Tyr Asn Ala Ser Asn Ser Gly Gly
290                 295                 300                 305

Tyr Phe Asp Met Arg Asn Ile Leu Asn Gly Ser Val Val Gln Lys His
                310                 315                 320

Pro Ile His Ala Val Thr Phe Val Asp Asn His Asp Ser Gln Pro Gly
            325                 330                 335

Glu Ala Leu Glu Ser Phe Val Gln Ser Trp Phe Lys Pro Leu Ala Tyr
            340                 345                 350

Ala Leu Ile Leu Thr Arg Glu Gln Gly Tyr Pro Ser Val Phe Tyr Gly
            355                 360                 365

Asp Tyr Tyr Gly Ile Pro Thr His Gly Val Pro Ser Met Lys Ser Lys
370                 375                 380                 385

Ile Asp Pro Leu Leu Gln Ala Arg Gln Thr Tyr Ala Tyr Gly Thr Gln
                390                 395                 400

His Asp Tyr Phe Asp His His Asp Ile Ile Gly Trp Thr Arg Glu Gly
            405                 410                 415

Asp Ser Ser His Pro Asn Ser Gly Leu Ala Thr Ile Met Ser Asp Gly
            420                 425                 430

Pro Gly Gly Asn Lys Trp Met Tyr Val Gly Lys His Lys Ala Gly Gln
            435                 440                 445

Val Trp Arg Asp Ile Thr Gly Asn Arg Ser Gly Thr Val Thr Ile Asn
450                 455                 460                 465

Ala Asp Gly Trp Gly Asn Phe Thr Val Asn Gly Gly Ala Val Ser Val
                470                 475                 480

Trp Val Lys Gln
            485

<210> SEQ ID NO 3
<211> LENGTH: 1753
<212> TYPE: DNA
<213> ORGANISM: Bacillus sp. KSM-K38
<220> FEATURE:
<221> NAME/KEY: sig_peptide
<222> LOCATION: (162)..(224)
<223> OTHER INFORMATION:
<221> NAME/KEY: mat_peptide
<222> LOCATION: (225)..()
<223> OTHER INFORMATION:
<221> NAME/KEY: CDS
<222> LOCATION: (162)..(1664)
<223> OTHER INFORMATION:

<400> SEQUENCE: 3
gtatgcgaaa cgatgcgcaa aactgcgcaa ctactagcac tcttcaggga ctaaaccacc      60
ttttttccaa aaatgacatc atataaacaa atttgtctac caatcactat ttaaagctgt     120
ttatgatata tgtaagcgtt atcattaaaa ggaggtattt g atg aga aga tgg gta    176
                                              Met Arg Arg Trp Val
                                                  -20 gta gca atg ttg gca gtg tta ttt tta ttt cct tcg gta gta gtt gca      224
Val Ala Met Leu Ala Val Leu Phe Leu Phe Pro Ser Val Val Val Ala
    -15                 -10                 -5                  -1
```

```
gat gga ttg aac ggt acg atg atg cag tat tat gag tgg cat ttg gaa      272
Asp Gly Leu Asn Gly Thr Met Met Gln Tyr Tyr Glu Trp His Leu Glu
 1               5                  10                  15 aac gac ggg cag cat tgg aat cgg ttg cac gat gat gcc gca gct ttg      320
Asn Asp Gly Gln His Trp Asn Arg Leu His Asp Asp Ala Ala Ala Leu
             20                  25                  30 agt gat gct ggt att aca gct att tgg att ccg cca gcc tac aaa ggt      368
Ser Asp Ala Gly Ile Thr Ala Ile Trp Ile Pro Pro Ala Tyr Lys Gly
         35                  40                  45 aat agt cag gcg gat gtt ggg tac ggt gca tac gat ctt tat gat tta      416
Asn Ser Gln Ala Asp Val Gly Tyr Gly Ala Tyr Asp Leu Tyr Asp Leu
     50                  55                  60 gga gag ttc aat caa aag ggt act gtt cga acg aaa tac gga act aag      464
Gly Glu Phe Asn Gln Lys Gly Thr Val Arg Thr Lys Tyr Gly Thr Lys
 65                  70                  75                  80 gca cag ctt gaa cga gct att ggg tcc ctt aaa tct aat gat atc aat      512
Ala Gln Leu Glu Arg Ala Ile Gly Ser Leu Lys Ser Asn Asp Ile Asn
                 85                  90                  95 gta tac gga gat gtc gtg atg aat cat aaa atg gga gct gat ttt acg      560
Val Tyr Gly Asp Val Val Met Asn His Lys Met Gly Ala Asp Phe Thr
             100                 105                 110 gag gca gtg caa gct gtt caa gta aat cca acg aat cgt tgg cag gat      608
Glu Ala Val Gln Ala Val Gln Val Asn Pro Thr Asn Arg Trp Gln Asp
         115                 120                 125 att tca ggt gcc tac acg att gat gcg tgg acg ggt ttc gac ttt tca      656
Ile Ser Gly Ala Tyr Thr Ile Asp Ala Trp Thr Gly Phe Asp Phe Ser
     130                 135                 140 ggg cgt aac aac gcc tat tca gat ttt aag tgg aga tgg ttc cat ttt      704
Gly Arg Asn Asn Ala Tyr Ser Asp Phe Lys Trp Arg Trp Phe His Phe
145                 150                 155                 160 aat ggt gtt gac tgg gat cag cgc tat caa gaa aat cat att ttc cgc      752
Asn Gly Val Asp Trp Asp Gln Arg Tyr Gln Glu Asn His Ile Phe Arg
                 165                 170                 175 ttt gca aat acg aac tgg aac tgg cga gtg gat gaa gag aac ggt aat      800
Phe Ala Asn Thr Asn Trp Asn Trp Arg Val Asp Glu Glu Asn Gly Asn
             180                 185                 190 tat gat tac ctg tta gga tcg aat atc gac ttt agt cat cca gaa gta      848
Tyr Asp Tyr Leu Leu Gly Ser Asn Ile Asp Phe Ser His Pro Glu Val
         195                 200                 205 caa gat gag ttg aag gat tgg ggt agc tgg ttt acc gat gag tta gat      896
Gln Asp Glu Leu Lys Asp Trp Gly Ser Trp Phe Thr Asp Glu Leu Asp
     210                 215                 220 ttg gat ggt tat cgt tta gat gct att aaa cat att cca ttc tgg tat      944
Leu Asp Gly Tyr Arg Leu Asp Ala Ile Lys His Ile Pro Phe Trp Tyr
225                 230                 235                 240 aca tct gat tgg gtt cgg cat cag cgc aac gaa gca gat caa gat tta      992
Thr Ser Asp Trp Val Arg His Gln Arg Asn Glu Ala Asp Gln Asp Leu
                 245                 250                 255 ttt gtc gta ggg gaa tat tgg aag gat gac gta ggt gct ctc gaa ttt     1040
Phe Val Val Gly Glu Tyr Trp Lys Asp Asp Val Gly Ala Leu Glu Phe
             260                 265                 270 tat tta gat gaa atg aat tgg gag atg tct cta ttc gat gtt cca ctt     1088
Tyr Leu Asp Glu Met Asn Trp Glu Met Ser Leu Phe Asp Val Pro Leu
         275                 280                 285 aat tat aat ttt tac cgg gct tca caa caa ggt gga agc tat gat atg     1136
Asn Tyr Asn Phe Tyr Arg Ala Ser Gln Gln Gly Gly Ser Tyr Asp Met
     290                 295                 300 cgt aat att tta cga gga tct tta gta gaa gcg cat ccg atg cat gca     1184
Arg Asn Ile Leu Arg Gly Ser Leu Val Glu Ala His Pro Met His Ala
305                 310                 315                 320
```

-continued

```
gtt acg ttt gtt gat aat cat gat act cag cca ggg gag tca tta gag      1232
Val Thr Phe Val Asp Asn His Asp Thr Gln Pro Gly Glu Ser Leu Glu
            325                 330                 335 tca tgg gtt gct gat tgg ttt aag cca ctt gct tat gcg aca att ttg      1280
Ser Trp Val Ala Asp Trp Phe Lys Pro Leu Ala Tyr Ala Thr Ile Leu
            340                 345                 350 acg cgt gaa ggt ggt tat cca aat gta ttt tac ggt gat tac tat ggg      1328
Thr Arg Glu Gly Gly Tyr Pro Asn Val Phe Tyr Gly Asp Tyr Tyr Gly
            355                 360                 365 att cct aac gat aac att tca gct aaa aaa gat atg att gat gag ctg      1376
Ile Pro Asn Asp Asn Ile Ser Ala Lys Lys Asp Met Ile Asp Glu Leu
    370                 375                 380 ctt gat gca cgt caa aat tac gca tat ggc acg cag cat gac tat ttt      1424
Leu Asp Ala Arg Gln Asn Tyr Ala Tyr Gly Thr Gln His Asp Tyr Phe
385                 390                 395                 400 gat cat tgg gat gtt gta gga tgg act agg gaa gga tct tcc tcc aga      1472
Asp His Trp Asp Val Val Gly Trp Thr Arg Glu Gly Ser Ser Ser Arg
                405                 410                 415 cct aat tca ggc ctt gcg act att atg tcg aat gga cct ggt ggt tcc      1520
Pro Asn Ser Gly Leu Ala Thr Ile Met Ser Asn Gly Pro Gly Gly Ser
            420                 425                 430 aag tgg atg tat gta gga cgt cag aat gca gga caa aca tgg aca gat      1568
Lys Trp Met Tyr Val Gly Arg Gln Asn Ala Gly Gln Thr Trp Thr Asp
            435                 440                 445 tta act ggt aat aac gga gcg tcc gtt aca att aat ggc gat gga tgg      1616
Leu Thr Gly Asn Asn Gly Ala Ser Val Thr Ile Asn Gly Asp Gly Trp
450                 455                 460 ggc gaa ttc ttt acg aat gga gga tct gta tcc gtg tac gtg aac caa      1664
Gly Glu Phe Phe Thr Asn Gly Gly Ser Val Ser Val Tyr Val Asn Gln
465                 470                 475                 480 taacaaaaag ccttgagaag ggattcctcc ctaactcaag gctttcttta tgtcgcttag    1724
cttaacgctt ctacgacttt gaagcttta                                      1753
```

<210> SEQ ID NO 4
<211> LENGTH: 501
<212> TYPE: PRT
<213> ORGANISM: Bacillus sp. KSM-K38

<400> SEQUENCE: 4

```
Met Arg Arg Trp Val Val Ala Met Leu Ala Val Leu Phe Leu Phe Pro
        -20                 -15                 -10

Ser Val Val Ala Asp Gly Leu Asn Gly Thr Met Met Gln Tyr Tyr
-5              -1  1               5                   10

Glu Trp His Leu Glu Asn Asp Gly Gln His Trp Asn Arg Leu His Asp
            15                  20                  25

Asp Ala Ala Leu Ser Asp Ala Gly Ile Thr Ala Ile Trp Ile Pro
        30                  35                  40

Pro Ala Tyr Lys Gly Asn Ser Gln Ala Asp Val Gly Tyr Gly Ala Tyr
    45                  50                  55

Asp Leu Tyr Asp Leu Gly Glu Phe Asn Gln Lys Gly Thr Val Arg Thr
60                  65                  70                  75

Lys Tyr Gly Thr Lys Ala Gln Leu Glu Arg Ala Ile Gly Ser Leu Lys
                80                  85                  90

Ser Asn Asp Ile Asn Val Tyr Gly Asp Val Val Met Asn His Lys Met
            95                  100                 105

Gly Ala Asp Phe Thr Glu Ala Val Gln Ala Val Gln Val Asn Pro Thr
        110                 115                 120
```

-continued

```
Asn Arg Trp Gln Asp Ile Ser Gly Ala Tyr Thr Ile Asp Ala Trp Thr
        125                 130                 135
Gly Phe Asp Phe Ser Gly Arg Asn Asn Ala Tyr Ser Asp Phe Lys Trp
140                 145                 150                 155
Arg Trp Phe His Phe Asn Gly Val Asp Trp Asp Gln Arg Tyr Gln Glu
                160                 165                 170
Asn His Ile Phe Arg Phe Ala Asn Thr Asn Trp Asn Trp Arg Val Asp
            175                 180                 185
Glu Glu Asn Gly Asn Tyr Asp Tyr Leu Leu Gly Ser Asn Ile Asp Phe
        190                 195                 200
Ser His Pro Glu Val Gln Asp Glu Leu Lys Asp Trp Gly Ser Trp Phe
    205                 210                 215
Thr Asp Glu Leu Asp Leu Asp Gly Tyr Arg Leu Asp Ala Ile Lys His
220                 225                 230                 235
Ile Pro Phe Trp Tyr Thr Ser Asp Trp Val Arg His Gln Arg Asn Glu
                240                 245                 250
Ala Asp Gln Asp Leu Phe Val Val Gly Glu Tyr Trp Lys Asp Asp Val
            255                 260                 265
Gly Ala Leu Glu Phe Tyr Leu Asp Glu Met Asn Trp Glu Met Ser Leu
        270                 275                 280
Phe Asp Val Pro Leu Asn Tyr Asn Phe Tyr Arg Ala Ser Gln Gln Gly
    285                 290                 295
Gly Ser Tyr Asp Met Arg Asn Ile Leu Arg Gly Ser Leu Val Glu Ala
300                 305                 310                 315
His Pro Met His Ala Val Thr Phe Val Asp Asn His Asp Thr Gln Pro
                320                 325                 330
Gly Glu Ser Leu Glu Ser Trp Val Ala Asp Trp Phe Lys Pro Leu Ala
            335                 340                 345
Tyr Ala Thr Ile Leu Thr Arg Glu Gly Gly Tyr Pro Asn Val Phe Tyr
        350                 355                 360
Gly Asp Tyr Tyr Gly Ile Pro Asn Asp Asn Ile Ser Ala Lys Lys Asp
    365                 370                 375
Met Ile Asp Glu Leu Leu Asp Ala Arg Gln Asn Tyr Ala Tyr Gly Thr
380                 385                 390                 395
Gln His Asp Tyr Phe Asp His Trp Asp Val Val Gly Trp Thr Arg Glu
                400                 405                 410
Gly Ser Ser Ser Arg Pro Asn Ser Gly Leu Ala Thr Ile Met Ser Asn
            415                 420                 425
Gly Pro Gly Gly Ser Lys Trp Met Tyr Val Gly Arg Gln Asn Ala Gly
        430                 435                 440
Gln Thr Trp Thr Asp Leu Thr Gly Asn Asn Gly Ala Ser Val Thr Ile
    445                 450                 455
Asn Gly Asp Gly Trp Gly Glu Phe Phe Thr Asn Gly Gly Ser Val Ser
460                 465                 470                 475
Val Tyr Val Asn Gln
            480
```

<210> SEQ ID NO 5
<211> LENGTH: 30
<212> TYPE: DNA
<213> ORGANISM: Artificial Sequence
<220> FEATURE:
<223> OTHER INFORMATION: Synthetic DNA

<400> SEQUENCE: 5
gagtcgacca gcacaagccc atcataatgg						30

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
taaagcttca atttatattg g							21

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gggtcgacca gcacaagccg atggattgaa cggtacgatg				40

<210> SEQ ID NO 8
<211> LENGTH: 29
<212> TYPE: DNA
<213> ORGANISM: Artificial Sequence
<220> FEATURE:
<223> OTHER INFORMATION: Synthetic DNA

<400> SEQUENCE: 8
taaagctttt gttattggtt cacgtacac						29

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA

<400> SEQUENCE: 9
ccagatctac ttaccatttt agagtca						27

<210> SEQ ID NO 10
<211> LENGTH: 34
<212> TYPE: DNA
<213> ORGANISM: Artificial Sequence
<220> FEATURE:
<223> OTHER INFORMATION: Synthetic DNA

<400> SEQUENCE: 10
atttgccaaa tgacgggcag cattggaatc ggtt					34

<210> SEQ ID NO 11
<211> LENGTH: 34
<212> TYPE: DNA
<213> ORGANISM: Artificial Sequence
<220> FEATURE:
<223> OTHER INFORMATION: Synthetic DNA

<400> SEQUENCE: 11
aaccgattcc aatgctgccc gtcatttggc aaat					34

<210> SEQ ID NO 12
<211> LENGTH: 34

```
<212> TYPE: DNA
<213> ORGANISM: Artificial Sequence
<220> FEATURE:
<223> OTHER INFORMATION: Synthetic DNA

<400> SEQUENCE: 12
tttgaatggc atttgtcaaa tgacggggaa ccac                        34

<210> SEQ ID NO 13
<211> LENGTH: 33
<212> TYPE: DNA
<213> ORGANISM: Artificial Sequence
<220> FEATURE:
<223> OTHER INFORMATION: Synthetic DNA

<400> SEQUENCE: 13
acaaggagtc agttggaagg tgccgtgaca tct                         33

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
cgaaaccaag taatatcagg t                                      21

<210> SEQ ID NO 15
<211> LENGTH: 27
<212> TYPE: DNA
<213> ORGANISM: Artificial Sequence
<220> FEATURE:
<223> OTHER INFORMATION: Synthetic DNA

<400> SEQUENCE: 15
aatacccatt ccgattttaa atggcgc                                27

<210> SEQ ID NO 16
<211> LENGTH: 33
<212> TYPE: DNA
<213> ORGANISM: Artificial Sequence
<220> FEATURE:
<223> OTHER INFORMATION: Synthetic DNA

<400> SEQUENCE: 16
gattgggatc agtcatgyca gcttcagaac aaa                         33

<210> SEQ ID NO 17
<211> LENGTH: 33
<212> TYPE: DNA
<213> ORGANISM: Artificial Sequence
<220> FEATURE:
<223> OTHER INFORMATION: Synthetic DNA

<400> SEQUENCE: 17
aaattcaccg gaaaggtatg ggactgggaa gta                         33

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 18
tcatccagat gtaatcaatg                                              20

<210> SEQ ID NO 19
<211> LENGTH: 33
<212> TYPE: DNA
<213> ORGANISM: Artificial Sequence
<220> FEATURE:
<223> OTHER INFORMATION: Synthetic DNA

<400> SEQUENCE: 19
cttagaaatt ggggagaatg gtatacaaat aca                               33

<210> SEQ ID NO 20
<211> LENGTH: 33
<212> TYPE: DNA
<213> ORGANISM: Artificial Sequence
<220> FEATURE:
<223> OTHER INFORMATION: Synthetic DNA

<400> SEQUENCE: 20
gtgaaacata ttaaatgcag ctatacgaga gat                               33

<210> SEQ ID NO 21
<211> LENGTH: 33
<212> TYPE: DNA
<213> ORGANISM: Artificial Sequence
<220> FEATURE:
<223> OTHER INFORMATION: Synthetic DNA

<400> SEQUENCE: 21
aacaccacag gtaaagaaat gtttgcagtt gca                               33

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
agaattttgg caaaatgacc t                                            21

<210> SEQ ID NO 23
<211> LENGTH: 26
<212> TYPE: DNA
<213> ORGANISM: Artificial Sequence
<220> FEATURE:
<223> OTHER INFORMATION: Synthetic DNA

<400> SEQUENCE: 23
ttgctgcaat ccataactat ttaaat                                       26

<210> SEQ ID NO 24
<211> LENGTH: 33
<212> TYPE: DNA
<213> ORGANISM: Artificial Sequence
<220> FEATURE:
<223> OTHER INFORMATION: Synthetic DNA

<400> SEQUENCE: 24
cttgctgcaa tcgaaagyta tttaaataaa aca                               33

<210> SEQ ID NO 25
<211> LENGTH: 33
```

```
<212> TYPE: DNA
<213> ORGANISM: Artificial Sequence
<220> FEATURE:
<223> OTHER INFORMATION: Synthetic DNA

<400> SEQUENCE: 25
ggctattttg atatggcaaa tattttaaat ggt                           33

<210> SEQ ID NO 26
<211> LENGTH: 21
<212> TYPE: DNA
<213> ORGANISM: Artificial Sequence
<220> FEATURE:
<223> OTHER INFORMATION: Synthetic DNA

<400> SEQUENCE: 26
tctgacaagg cagcaaggtt a                                       21

<210> SEQ ID NO 27
<211> LENGTH: 27
<212> TYPE: DNA
<213> ORGANISM: Artificial Sequence
<220> FEATURE:
<223> OTHER INFORMATION: Synthetic DNA

<400> SEQUENCE: 27
gatccacttc tggaagcacg tcaaacg                                 27

<210> SEQ ID NO 28
<211> LENGTH: 27
<212> TYPE: DNA
<213> ORGANISM: Artificial Sequence
<220> FEATURE:
<223> OTHER INFORMATION: Synthetic DNA

<400> SEQUENCE: 28
gggggtaata aagaatgta tgtcggg                                  27

<210> SEQ ID NO 29
<211> LENGTH: 26
<212> TYPE: DNA
<213> ORGANISM: Artificial Sequence
<220> FEATURE:
<223> OTHER INFORMATION: Synthetic DNA

<400> SEQUENCE: 29
atgtatgtcg ggcgacataa agctgg                                  26

<210> SEQ ID NO 30
<211> LENGTH: 25
<212> TYPE: DNA
<213> ORGANISM: Artificial Sequence
<220> FEATURE:
<223> OTHER INFORMATION: Synthetic DNA

<400> SEQUENCE: 30
gatggttggg gggatttcac tgtaa                                   25

<210> SEQ ID NO 31
<211> LENGTH: 27
<212> TYPE: DNA
<213> ORGANISM: Artificial Sequence
<220> FEATURE:
<223> OTHER INFORMATION: Synthetic DNA
```

<400> SEQUENCE: 31
ttcactgtaa acgatggggc agtttcg                                    27

<210> SEQ ID NO 32
<211> LENGTH: 21
<212> TYPE: DNA
<213> ORGANISM: Artificial Sequence
<220> FEATURE:
<223> OTHER INFORMATION: Synthetic DNA

<400> SEQUENCE: 32
ggtttgggtg cagcaataaa t                                          21

<210> SEQ ID NO 33
<211> LENGTH: 33
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (16)..(18)
<223> OTHER INFORMATION: n = a, c, t, or g

<400> SEQUENCE: 33
tttgaatggc atttgnnnaa tgacgggaac cac                             33

<210> SEQ ID NO 34
<211> LENGTH: 33
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (16)..(18)
<223> OTHER INFORMATION: n = a, c, t, or g

<400> SEQUENCE: 34
aaattcaccg gaaagnnntg ggactgggaa gta                             33

<210> SEQ ID NO 35
<211> LENGTH: 33
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (16)..(18)
<223> OTHER INFORMATION: n = a, c, t, or g

<400> SEQUENCE: 35
gtgaaacata ttaaannnag ctatacgaga gat                             33

<210> SEQ ID NO 36
<211> LENGTH: 33
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (16)..(18)
<223> OTHER INFORMATION: n = a, c, t, or g

<400> SEQUENCE: 36
cttgctgcaa tcgaannnta tttaaataaa aca                             33

<210> SEQ ID NO 37
<211> LENGTH: 25

```
<212> TYPE: DNA
<213> ORGANISM: Artificial Sequence
<220> FEATURE:
<223> OTHER INFORMATION: Synthetic DNA

<400> SEQUENCE: 37
gatggttggg gggaattcac tgtaa                                              25

<210> SEQ ID NO 38
<211> LENGTH: 39
<212> TYPE: DNA
<213> ORGANISM: Artificial Sequence
<220> FEATURE:
<223> OTHER INFORMATION: Synthetic DNA

<400> SEQUENCE: 38
ccaacgaatc gttggcaggt aatttcaggt gcctacacg                               39

<210> SEQ ID NO 39
<211> LENGTH: 33
<212> TYPE: DNA
<213> ORGANISM: Artificial Sequence
<220> FEATURE:
<223> OTHER INFORMATION: Synthetic DNA

<400> SEQUENCE: 39
attgatgcgt ggacgagttt cgactttca ggg                                      33

<210> SEQ ID NO 40
<211> LENGTH: 21
<212> TYPE: DNA
<213> ORGANISM: Artificial Sequence
<220> FEATURE:
<223> OTHER INFORMATION: Synthetic DNA

<400> SEQUENCE: 40
tttcgacttt ccagggcgta a                                                  21

<210> SEQ ID NO 41
<211> LENGTH: 43
<212> TYPE: DNA
<213> ORGANISM: Artificial Sequence
<220> FEATURE:
<223> OTHER INFORMATION: Synthetic DNA

<400> SEQUENCE: 41
ggtgttgact gggatcagca atatcaagaa aatcatattt tcc                          43

<210> SEQ ID NO 42
<211> LENGTH: 42
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (27)..(27)
<223> OTHER INFORMATION: n = a, c, t, or g

<400> SEQUENCE: 42
catattttcc gctttgcaaa tacggtntgg aacaggcgag tg                           42

<210> SEQ ID NO 43
<211> LENGTH: 44
<212> TYPE: DNA
<213> ORGANISM: Artificial Sequence
<220> FEATURE:
<223> OTHER INFORMATION: Synthetic DNA
```

```
<400> SEQUENCE: 43
aatatcgact ttagtcatcc agatgtacaa gatgagttga agga              44

<210> SEQ ID NO 44
<211> LENGTH: 43
<212> TYPE: DNA
<213> ORGANISM: Artificial Sequence
<220> FEATURE:
<223> OTHER INFORMATION: Synthetic DNA

<400> SEQUENCE: 44
gacgtaggtg ctctcgaatc ttatttagat gaaatgaatt ggg               43

<210> SEQ ID NO 45
<211> LENGTH: 21
<212> TYPE: DNA
<213> ORGANISM: Artificial Sequence
<220> FEATURE:
<223> OTHER INFORMATION: Synthetic DNA

<400> SEQUENCE: 45
cgataacatt ccagctaaaa a                                       21

<210> SEQ ID NO 46
<211> LENGTH: 38
<212> TYPE: DNA
<213> ORGANISM: Artificial Sequence
<220> FEATURE:
<223> OTHER INFORMATION: Synthetic DNA

<400> SEQUENCE: 46
gacctggtgg ttccaagaga atgtatgtag gacgtcag                     38

<210> SEQ ID NO 47
<211> LENGTH: 42
<212> TYPE: DNA
<213> ORGANISM: Artificial Sequence
<220> FEATURE:
<223> OTHER INFORMATION: Synthetic DNA

<400> SEQUENCE: 47
aatggcgatg gatggggcga tttctttacg aatggaggat ct                42

<210> SEQ ID NO 48
<211> LENGTH: 39
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (19)..(21)
<223> OTHER INFORMATION: n = a, c, t, or g

<400> SEQUENCE: 48
ccaacgaatc gttggcagnn natttcaggt gcctacacg                    39

<210> SEQ ID NO 49
<211> LENGTH: 33
<212> TYPE: DNA
<213> ORGANISM: Artificial Sequence
<220> FEATURE:
<223> OTHER INFORMATION: Synthetic DNA

<400> SEQUENCE: 49
gttgactggg atgagcgcaa acaagaaaat cat                          33
```

-continued

```
<210> SEQ ID NO 50
<211> LENGTH: 25
<212> TYPE: DNA
<213> ORGANISM: Artificial Sequence
<220> FEATURE:
<223> OTHER INFORMATION: Synthetic DNA

<400> SEQUENCE: 50
tggatgaaga gttcggtaat tatga                                        25

<210> SEQ ID NO 51
<211> LENGTH: 33
<212> TYPE: DNA
<213> ORGANISM: Artificial Sequence
<220> FEATURE:
<223> OTHER INFORMATION: Synthetic DNA

<400> SEQUENCE: 51
agtcatccag aggtcgtaga tgagttgaag gat                               33
```

HIGHLY PRODUCTIVE ALPHA-AMYLASES

TECHNICAL FIELD

The present invention relates to mutant α-amylases having improved productivity.

BACKGROUND ART

α-Amylases [EC.3.2.1.1.] have been used in a wide range of industrial fields such as starch industry, brewing industry, fiber industry, pharmaceutical industry and food industry. Among them, those capable of degrading starches at high random are suited for detergents. Conventionally known as such are, as well as α-amylases derived from *Bacillus licheniformis*, liquefying alkaline α-amylases derived from the alkaliphilic strain Bacillus sp. KSM-AP1378 (FERM BP-3048) (WO94/26881) and improved enzymes having improved heat resistance and oxidant resistance (WO98/44126).

The present inventors have recently found liquefying alkaline α-amylases derived from the alkaliphilic strain Bacillus sp. KSM-K38 (FERM BP-6946) and having chelating-agent- and oxidation-resistance (Japanese Patent Application No. Hei 10-362487, Japanese Patent Application No. Hei 10-362488); and improved enzymes having improved heat resistance (Japanese Patent Application No. Hei 11-163569).

In addition to such properties, enzymes for detergents are required to have high productivity in consideration of their industrial production. Although various trials have been made to improve the heat resistance or oxidant resistance of α-amylases for detergent by using protein engineering technique, neither improvement of productivity has been considered sufficiently nor an attempt of production increase by mutation of a structural gene has been reported yet.

An object of the present invention is to provide mutant α-amylases having excellent productivity.

DISCLOSURE OF THE INVENTION

The present inventors introduced, in microorganisms, mutant α-amylase structural gene constructed by site-directed mutagenesis and evaluated productivity of α-amylases. As a result, it has been found that since an α-amylase gene has a site taking part in the improvement of productivity, introduction, into a microorganism, of a recombinant gene having this site mutated makes it possible to produce α-amylases having drastically improved productivity.

In one aspect of the present invention, there is thus provided a mutant α-amylase which is derived from an α-amylase having an amino acid sequence represented by SEQ ED No. 2 or showing at least 60% homology thereto by substitution or deletion of at least one amino acid residue corresponding to any one of $Pro_{18}$, $Gln_{86}$, $Glu_{130}$, $Asn_{154}$, $Arg_{171}$, $Ala_{186}$, $Glu_{212}$, $Val_{222}$, $Tyr_{243}$, $Pro_{260}$, $Lys_{269}$, $Glu_{276}$, $Asn_{277}$, $Arg_{310}$, $Glu_{360}$, $Gln_{391}$, $Trp_{439}$, $Lys_{444}$, $Asn_{471}$ and $Gly_{476}$ of the amino acid sequence.

In another aspect of the present invention, there is also provided a mutant α-amylase derived from an α-amylase having an amino acid sequence represented by SEQ ID No. 4 or showing at least 60% homology thereto by substitution or deletion of at least one amino acid residue corresponding to any one of $Asp_{128}$, $Gly_{140}$, $Ser_{144}$, $Arg_{168}$, $Asn_{181}$, $Glu_{207}$, $Phe_{272}$, $Ser_{375}$, $Trp_{434}$ and $Glu_{466}$ of the amino acid sequence.

In a further aspect of the present invention, there is also provided a gene encoding this mutant α-amylase, a vector containing the gene, a cell transformed with the vector and a production method of a mutant α-amylase which comprises cultivating the transformed cell.

In a still further aspect of the present invention, there is also provided a detergent composition containing this mutant α-amylase.

BEST MODE FOR CARRYING OUT THE INVENTION

Figure 1:
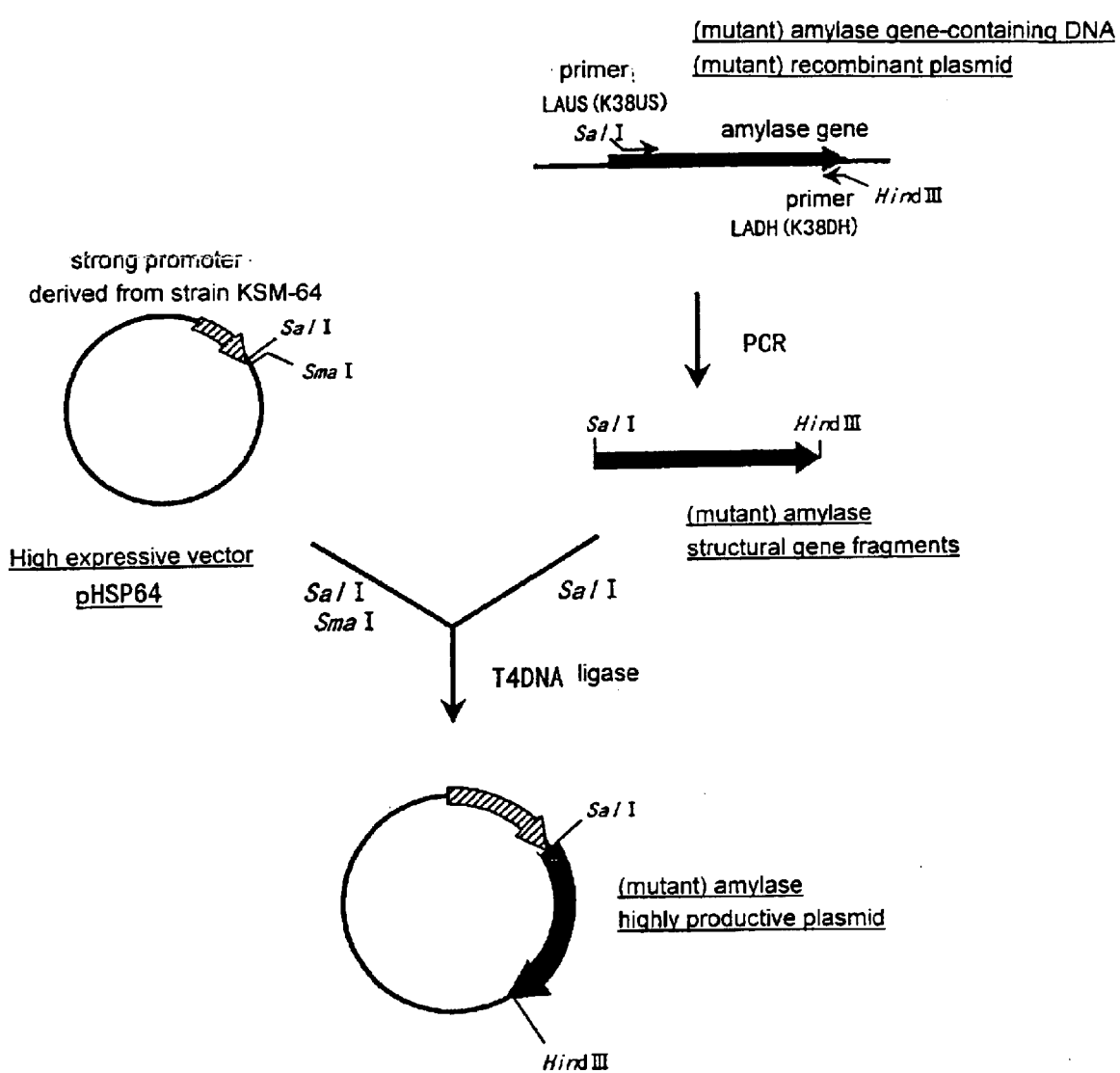
FIG. 1 illustrates a method of constructing a recombinant plasmid for production of an α-amylase derived from the strain KSM-1378 or KSM-K38.

The term "highly productive mutant α-amylase" as used herein means an α-amylase whose yield is increased, upon production of it by cultivating a recombinant microorganism, by at least 5%, preferably at least 10%, more preferably at least 20% compared with that before mutation.

The mutant α-amylase of the present invention is constructed so that out of amino acids constituting the α-amylase, the amino acid residues taking part in the productivity are substituted with another amino acid residues or deleted. Examples of the α-amylase usable here include liquefying α-amylases derived from *Bacillus. amyloliquefaciens* or *Bacillus. licheniformis* and liquefying alkaline α-amylases derived from alkaliphilic microorganisms belonging to the Bacillus sp., of which α-amylases having an amino acid sequence represented by SEQ ID No. 2 or SEQ ID No. 4 and α-amylases having at least 60% homology to the above-described amino acid sequence are preferred.

Examples of the α-amylase having the amino acid sequence represented by SEQ ID NO. 2, or α-amylase having at least 60% homology thereto include liquefying alkaline α-amylases derived from the strain Bacillus sp. KSM-AF1378 (FERM BP-3048) (Japanese Patent Application. Laid-Open No. Hei 8-336392) and improved enzymes of the above-described one in heat resistance and oxidant resistance which are constructed by protein engineering technique (WO98/44126).

Examples of the α-amylase having the amino acid sequence represented by SEQ ID No. 4 or having at least 60% homology thereto include liquefying alkaline α-amylases derived from the strain Bacillus sp. KSM-K38 (FERM BP-6946) and improved enzymes of the above-described one in heat resistance which are constructed by protein engineering technique (Japanese Patent Application No. Hei 11-163569).

The homology of an amino acid sequence is calculated by Lipman-Pearson method (Science, 227, 1435(1985)).

The mutant α-amylase of the present invention can be obtained first by cloning, from a microorganism producing an α-amylase, a gene encoding the α-amylase. For this purpose, ordinarily employed gene recombinant technique, for example, the method as described in Japanese Patent Application Laid-Open No. Hei 8-336392 may be employed. Examples of the gene usable here include that represented by from the above-described ones and having improved heat resistance and oxidant resistance are also usable.

For mutation of the gene thus obtained by cloning, any site-directed mutagenesis ordinarily employed can be adopted. For example, mutation can be conducted using a "Site-Directed Mutagenesis System Mutan-Super Express Km" kit (product of Takara Shuzo Co., Ltd.).

Mutation for obtaining highly productive α-amylases of the invention can be attained, for example, by substitution or deletion, in an α-amylase having an amino acid sequence represented by SEQ ID No. 2 or having at least 60% homology thereto, of at least one amino acid residue corresponding to any one of $Pro_{18}$, $Gln_{86}$, $Glu_{130}$, $Asn_{154}$, $Arg_{171}$, $Ala_{186}$, $Glu_{212}$, $Val_{222}$, $Tyr_{243}$, $Pro_{260}$, $Lys_{269}$, $Glu_{276}$, $Asn_{277}$, $Arg_{310}$, $Glu_{360}$, $Gln_{391}$, $Trp_{439}$, $Lys_{444}$, $Asn_{471}$ and $Gly_{476}$ of the amino acid sequence; or by substitution or deletion, in another α-amylase having an amino acid sequence represented by SEQ ID No.4 or having at least 60% homology thereto, of at least one amino acid residue corresponding to any one of $Asp_{128}$, $Gly_{140}$, $Ser_{144}$, $Arg_{168}$, $Asn_{181}$, $Glu_{207}$, $Phe_{272}$, $Ser_{375}$, $Trp_{434}$ and $Glu_{466}$ of the amino acid sequence. Preferred mutations include, in the amino acid sequence of SEQ ID No. 2 substitution of the amino acid residue corresponding to $Pro_{18}$ with Ser or Thr, the amino acid residue corresponding to $Gln_{86}$ with Glu, the amino acid residue corresponding to $Glu_{130}$ with Val or Gln, the amino acid residue corresponding to $Asn_{154}$ with Asp, the amino acid residue corresponding to $Arg_{171}$ with Cys or Gln, the amino acid residue corresponding to $Ala_{186}$ with Val or Asn, the amino acid residue corresponding to $Glu_{212}$ with Asp, the amino acid residue corresponding to $Val_{222}$ with Gln, the amino acid residue corresponding to $Tyr_{243}$ with Cys or Ser, the amino acid residue corresponding to $Pro_{260}$ with Glu, the amino acid residue corresponding to $Lys_{269}$, with Gln, the amino acid residue corresponding to $Glu_{276}$ with His, the amino acid residue corresponding to $Asn_{277}$ with Ser or Phe, the amino acid residue corresponding to $Arg_{310}$ with Ala, the amino acid residue corresponding to $Glu_{360}$ with Gln, the amino acid residue corresponding to $Gln_{391}$ with Glu, the amino acid residue corresponding to $Trp_{439}$ with Arg, the amino acid residue corresponding to $Lys_{444}$ with Arg, the amino acid residue corresponding to $Asn_{471}$, with Asp or Glu, or the amino acid residue corresponding to $Gly_{476}$ with Asp;

or substitution, in the amino acid sequence of SEQ ID No. 4, of the amino acid residue corresponding to $Asp_{128}$ with Val or Gln, the amino acid residue corresponding to $Gly_{140}$ with Ser, the amino acid residue corresponding to $Ser_{144}$ with Pro, the amino acid residue corresponding to $Arg_{168}$ with Gln, the amino acid residue corresponding to $Gln_{181}$, with Val, the amino acid residue corresponding to $Glu_{270}$ with Asp, the amino acid residue corresponding to $Phe_{272}$ with Ser, the amino acid residue corresponding to $Ser_{375}$ with Pro, the amino acid residue corresponding to $Trp_{434}$ with Arg or the amino acid residue corresponding to $Glu_{466}$ with Asp.

Among the mutations of the amino acid sequence of SEQ ID No. 2, those by substitution of the amino acid residue corresponding to $Gln_{86}$ with Glu, the amino acid residue corresponding to $Glu_{130}$ with Val or Gln, the amino acid residue corresponding to $Ala_{186}$ with Asn, the amino acid residue corresponding to $Tyr_{243}$ with Ser, the amino acid residue corresponding to $Pro_{260}$ with Glu, the amino acid residue corresponding to $Lys_{269}$ with Gln, the amino acid residue corresponding to $Asn_{277}$ with Phe and the amino acid residue corresponding to $Asn_{471}$ with Asp or Gln can bring about improvement in solubility of the α-amylase in a culture medium or desalted and concentrated solution thereof. More specifically, the above-described mutations make it possible to improve the residual activity of the αamylase in the supernatant after storage at 4° C. for one week in a desalted and concentrated solution by at least 5%, especially 10% compared with the activity before mutation. Accordingly, in the case of the mutant α-amylases of the present invention obtained by such amino acid mutations, a fermented concentrate solution of a high concentration is available at a high yield and enzyme formulation treatment such as ultrafiltration after fermentation production can be conducted efficiently.

A combination of two or more substitutions or deletions of various amino acid residues is also effective for such amino acid mutations. It is also possible to use the above-exemplified mutation in combination with a mutation for improving enzymatic properties, for example, in an α-amylase having an amino acid sequence represented SEQ ID No. 2 or having at least 60% homology thereto, a mutation for improving heat resistance by deleting amino acid residues corresponding to $Arg_{181}$ and $Gly_{182}$, a mutation for improving oxidant resistance by substituting the amino acid residue corresponding to $Met_{222}$ with Thr or a mutation for improving solubility by substituting the amino acid residue corresponding $Lys_{484}$ with Gln; or in an α-amylase having an amino acid sequence represented by SEQ ID No. 4 or having at least 60% homology thereto, a mutation for further reinforcing oxidant resistance by substituting the amino acid residue corresponding to $Met_{107}$ with Leu or a mutation for heightening detergency of a laundry detergent by substituting the amino acid residue corresponding $Glu_{188}$ with Ile.

A mutant α-amylase is available at a high yield by appropriately combining a mutant α-amylase structural gene with a control gene and a proper plasmid vector, thereby constructing a plasmid for the production of the α-amylase, introducing the resulting plasmid into a microorganism such as *Bacillus subtilis* or *Escherichia coli*, preferably, *Bacillus subtilis* and cultivating the resulting recombinant microorganism.

The mutant α-amylase thus obtained has improved productivity by about 10 to 500% as shown later in Examples while maintaining biochemical properties as an enzyme, thus having excellent properties. By the above-described mutation of the amino acid residues of liquefying alkaline α-amylases having heat resistance, chelating agent resistance, oxidant resistance and high solubility, it is therefore possible to create useful enzymes having drastically improved productivity in a recombinant microorganism without losing the above-described original properties.

The detergent compositions of the present invention may contain, in addition to the α-amylase of the invention, one or more than one enzymes selected from debranching enzymes (such as pullulanase, isoamylase and neopullulanase), α-glucosidase, glucoamylase, protease, cellulase, lypase, pectinase, protopectinase, pectate lyase, peroxidase, laccase and catalase.

The detergent composition may contain, in addition, components ordinarily added to a detergent, for example, surfactants such as anionic surfactants, amphoteric surfactants, nonionic surfactants and cationic surfactants, chelating agents, alkali agents, inorganic salts, anti-redeposition agents, chlorine scavengers, reducing agents, bleaching agents, fluorescent dye solubilizing agents, perfumes, anti-caking agents, enzyme activating agents, antioxidants, antiseptics, blueing agents, bleach activating agents, enzyme stabilizing agents and regulator.

The detergent compositions of the invention can be produced in a manner known per se in the art from a combination of the highly productive α-amylase available by the above-described method and the above-described known detergent components. The form of the detergent can be selected according to the using purpose and examples include liquid, powder and granule. The detergent compositions of the present invention are suited as laundry detergents, bleaching detergents, detergents for automatic dish washer, pipe cleaners, and artificial tooth cleaners, of which they are especially suited as laundry detergents, bleaching detergents and detergents for automatic dish washer.

The highly productive mutant α-amylases of the invention are also usable as starch liquefying saccharifying compositions. Moreover, these mutant α-amylases, after addition thereto of one or more than one enzymes selected from glucoamylase, maltase, pullulanase, isoamylase and neopullulanase, can be allowed to act on starches.

Furthermore, the mutant α-amylases of the present invention are usable as a desizing composition of fibers and an enzyme such as pullulanase, isoamylase or neopullulanase can be incorporated in the composition.

EXAMPLES

Measurement of Amylase Activity and Protein Content

Amylase activity and protein content of the enzymes each produced from recombinant *Bacillus subtilis* were measured in accordance with the below-described methods.

Amylase activity was measured by the 3,5-dinitrosalicylic acid method (DNS method). After reaction at 50° C. for 15 minutes in a reaction mixture of a 40 mM glycine-sodium hydroxide buffer (pH 10) containing soluble starch, the reducing sugar thus formed was quantitatively analyzed by the DNS method. As the titer of the enzyme, the amount of the enzyme which formed reducing sugar equivalent to 1 μmol of glucose in one minute was defined as one unit.

The protein content was determined by "Protein Assay Kit" (product of Bio-Rad Laboratories) using bovine serum albumin as standard.

Referential Example 1
Screening of Liquefying Alkaline Amylase

About 0.5 g of soil was suspended in sterilized water and the resulting suspension was heat treated at 80° C. for 15 minutes. The supernatant of the heat treated mixture was diluted with an adequate amount of sterilized water, followed by applying to an isolating agar medium (Medium A). The medium was then cultured at 30° C. for 2 days to grow colonies. The colonies which formed transparent zones in their peripheries due to starch dissolution were selected and isolated as amylase producing strains. The resulting isolated strains were inoculated in Medium B, followed by aerobic shaken culture at 30° C. for 2 days. After cultivation, the chelating agent (EDTA) resisting capacity of the supernatant obtained by centrifugation was measured and in addition, the optimum working pH was measured. Thus, strain Bacillus sp. KSM-K38 (FERM BP-6946) was obtained.

| Medium A: | Tryptone | 1.5% |
|---|---|---|
| | Soytone | 0.5% |
| | Sodium chloride | 0.5% |
| | Colored starch | 0.5% |
| | Agar | 1.5% |
| | $Na_2Co_3$ | 0.5% |
| | (pH 10) | |
| Medium B: | Tryptone | 1.5% |
| | Soytone | 0.5% |
| | Sodium chloride | 0.5% |
| | Soluble starch | 1.0% |
| | $Na_2CO_3$ | 0.5% |
| | (pH 10) | |

The mycological properties of strain KSM-K38 are shown in Table 1.

TABLE 1

| Strain KSM-K38 | |
|---|---|
| (a) Observation under microscope | Cells are rods of a size of 1.0 to 1.2 μm × 2.4 to 5.4 μm in the strain K36 and 1.0 to 1.2 μm × 1.8 to 3.8 μm in the strain K38, and form an elliptical endospore (1.0 to 1.2 μm × 1.2 to 1.4 μm) at their subterminals or center. They have flagella and are motile. Gram's staining is positive. Acid fastness: negative. |
| (b) Growth in various culture mediums. The strains are alikaliphilic so that 0.5% sodium carbonate was added to the culture medium in the tests described hereinafter. | |
| Nutrient agar plate culture | Growth of cells is good. Colony has a circular shape, with its surface being smooth and its peripheral end being smooth. The color of the colony is yellowish brown. |
| Nutrient agar slant culture | Cells can grow. |
| Nutrient broth | Cells can grow. |
| Stab culture in nutrient-broth gelatin | Growth of cells is good. Liquefaction of gelatin is not observed. |
| Litmus milk medium | No change in growth. |
| (c) Physiological properties | |
| Nitrate reduction and denitrification | Nitrate reduction: positive Denitrification: negative |
| MR test | Indeterminable because the medium is an alkaline medium. |
| V-P test | Negative |
| Production of indole | Negative |
| Production of hydrogen sulfide | Negative |
| Hydrolysis of starch | Positive |
| Utilization of citric acid | Positive in Christensen's medium but negative in Koser's medium and Simmon's medium. |

TABLE 1-continued

Strain KSM-K38

| | |
|---|---|
| Utilization of inorganic nitrogen sources | Nitrate is utilized but ammonium salts are not. |
| Production of colorants | Negative |
| Urease | Negative |
| Oxidase | Negative |
| Catalase | Positive |
| Growth range | Growth temperature range: 15 to 40° C., optimum growth temperature: 30° C., growth pH range: pH 9.0 to 11.0, optimum growth pH range: same |
| Behavior on oxygen | Aerobic |
| O-F test | Cells do not grow |
| Sugar utilization | L-galactose, D-xylose, L-arabinose, lactose, glycerin, melibiose, ribose, D-glucose, D-mannose, maltose, sucrose, trehalose, D-mannitol, starch, raffinose and D-fructose are utilized. |
| Growth in a salt-containing medium | Cells can grow when salt concentration is 12%, but not when salt concentration is 15%. |

Referential Example 2
Cultivation of Strain KSM-K38

In the liquid medium B of Referential Example 1, the strain KSM-K38 was inoculated, followed by aerobic shaken culture at 30° C. for 2 days. The amylase activity (at pH 8.5) of each of the supernatants isolated by centrifugation was measured. As a result, the activity in 1 L of the culture medium was found to be 1177 U.

Referential Example 3
Purification of Liquefying Alkaline Amylase

Ammonium sulfate was added to the supernatant of the culture medium of the strain KSM-K38 obtained in Referential Example 2 to give 80% saturation, followed by stirring. The precipitate thus formed was collected and dissolved in a 10 mM tris-HCl buffer (pH 7.5) containing 2 mM $CaCl_2$ to dialyze the resulting solution against the buffer overnight. The dialysate was loaded on a DEAE-Toyopearl 650M column equilibrated with the same buffer and protein was eluted in a linear gradient of 0 to 1 M of NaCl in the same buffer. The active fraction obtained by gel filtration column chromatography after dialysis against the same buffer was dialyzed against the buffer, whereby purified enzyme exhibited a single band on polyacrylamide gel electrophoresis (gel concentration: 10%) and sodium dodecylsulfate (SDS) electrophoresis was obtained.

Referential Example 4
Enzymological Properties

The properties of the purified enzyme are as follows:
(1) Action

It acts on starch, amylose, amylopectin and α-1,4-glycoside bond which is a partially degraded product thereof to degrade them and produce, from amylose, glucose (G1), maltose (G2), maltotriose (G3), maltotetraose (G4), maltopentaose (G5), maltohexaose (G6) and maltoheptaose (G7). But it does not act on pullulan.

(2) pH Stability (Britton-Robinson Buffer)

It exhibits residual activity of 70% or more within a range of pH 6.5 to 11.0 under treating conditions at 40° C. for 30 minutes.

(3) Working Temperature Range and Optimum Working Temperature

It acts in a wide temperature range of from 20 to 80° C., with the optimum working temperature being 50 to 60° C.

(4) Temperature Stability

The temperature at which the enzyme loses its activity was examined by causing a temperature change in a 50 mM glycine-sodium hydroxide buffer (pH 10) and then, treating at each temperature for 30 minutes. The residual activity of the enzyme is 80% or more at 40° C. and about 60% even at 45° C.

(5) Molecular Weight

The molecular weight as measured by sodium-dodecylsulfate polyacrylamide gel electrophoresis is 55,000 ±5,000.

(6) Isoelectric Point

Its isoelectric point as measured by isoelectric focusing electrophoresis is about 4.2.

(7) Effects of Surfactants

It is almost free from activity inhibition (activity remaining ratio: 90% or more) even when treated at pH 10 and 30° C. for 30 minutes in a 0.1% solution of a surfactant such as sodium linear alkylbenzene sulfonate, alkyl sulfate ester sodium salt, polyoxyethylene alkylsulfate ester sodium salt, sodium α-olefin sulfonate, sodium α-sulfonated fatty acid ester, sodium alkylsulfonate, SDS, soap and softanol.

(8) Effects of Metal Salts

It was treated at pH 10 and 30° C. for 30 minutes in each of the reaction systems containing various metal salts and their effects were studied. Its activity is inhibited by 1 mM of $Mn^{2+}$ (inhibition ratio: about 75%) and slightly inhibited by 1 mM of $Sr^{2+}$ and $Cd^{2+}$ (inhibition ratio: about 30%).

Example 1
Preparation of Various Recombinant Plasmids Having an α-Amylase Gene Ligated Thereto In accordance with the method as described in WO98/44126, genes encoding a mutant α-amylase (which will hereinafter be described as "ΔRG") having improved heat resistance and a mutant α-amylase ("ΔRG-M202T") having improved oxidant resistance as well as improved heat resistance were constructed, respectively, by deleting $Arg_{181}$ and $Gly_{182}$ of the α-amylase ("LAMY") which was derived from the strain Bacillus sp. KSM-AP1378 (FERM BP-3048) and had the amino acid sequence represented by SEQ ID No. 2; and by, in addition to this mutation by deletion, substituting Thr for $Met_{202}$ of the amino acid sequence represented by SEQ ID No. 2. With the genes as a template, gene fragments (about 1.5 kb) encoding these mutant α-amylases were amplified by the PCR reaction using primers LAUS (SEQ ID No. 5) and LADH (SEQ ID No. 6). After cutting of them with a restriction enzyme SalI, each of the fragments was inserted into the SalI-SmaI site of an expression vector pHSP64 (Japanese Patent Application Laid-Open No. Hei 6-217781), whereby a recombinant plasmid having a structural gene of each of the mutant α-amylases bonded thereto was constructed downstream of a strong promoter derived from an alkaline cellulase gene of the strain Bacillus sp. KSM-64 (FERM P-10482).

In the meantime, with a chromosomal DNA, which had been extracted from the cells of the strain Bacillus sp. KSM-K38 (FERM BP-6946) by the method of Saito and Miura (Biochim. Biophys. Acta, 72, 619 (1961)), as a template, PCR reaction was effected using primers K38US (SEQ ID No. 7) and K38DH (SEQ ID No. 8) shown in Table 2, whereby a structural gene fragment (about 1.5 kb) encoding an α-amylase (which will hereinafter be described as "K38AMY") having an amino acid sequence of SEQ ID No.4 was amplified. After cutting of it with a restriction enzyme SalI, the resulting fragment was inserted into the SalI-SmaI site of an expression vector pHSP64 to construct, downstream of a strong promoter derived from an alkaline cellulase gene of the strain Bacillus sp. KSM-64 (FERM P-10482) contained in pHSP64, a recombinant plasmid having a structural gene of K38AMY bonded thereto (FIG. 1). With this recombinant plasmid as a template, PCR reaction was effected using the primers CLUBG (SEQ ID. No. 9) and K38DH (SEQ. ID. No.8) to amplify a gene fragment (about 2.1 kb) having the strong promoter and K38AMY bonded thereto.

By the recombinant PCR method as described below, a gene encoding chimeric α-amylase between K38AMY and LAMY was constructed. Described specifically, with a chromosomal DNA of the strain K.SM-K38 (FERM BP6946) as a template, PCR reaction was conducted using primers K38DH (SEQ ID No. 8) and LA-K38 (SEQ ID No. 10) shown in Table 2, whereby a fragment encoding the sequence from $Gln_{20}$ downstream to the C-terminal of the amino acid sequence of K38AMY represented by SEQ ID No. 4 was amplified. With the above-described recombinant plasmid containing the LAMY gene and strong promoter as a template, PCR reaction was conducted using primers CLUBG (SEQ ID No. 9) and LA-K38R (SEQ ID No. 11) shown in Table 2, whereby a gene fragment encoding from the upstream strong promoter to $Gly_{21}$ of the amino acid sequence of LAMY of SEQ ID No. 2 was amplified. By the second PCR reaction using the resulting two DNA fragments and primers CLUBG (SEQ ID No. 9) and K38DH (SEQ ID No. 8) shown in Table 2, the resulting two fragments having, at the end thereof, complementary sequences derived from primers LA-K38 (SEQ ID No. 10) and LA-K38R (SEQ ID No. 11) respectively were combined, whereby a gene fragment (about 2.1 kb) encoding a chimeric α-amylase (which will hereinafter be described as "LA-K38AMY") which has, successively bonded thereto, a region encoding from $His_1$ to $Gly_{21}$ of the LAMY downstream of the strong promoter and a region encoding from $Gln_{20}$ to the C-terminal of the K38AMY was amplified.

Figure 2:
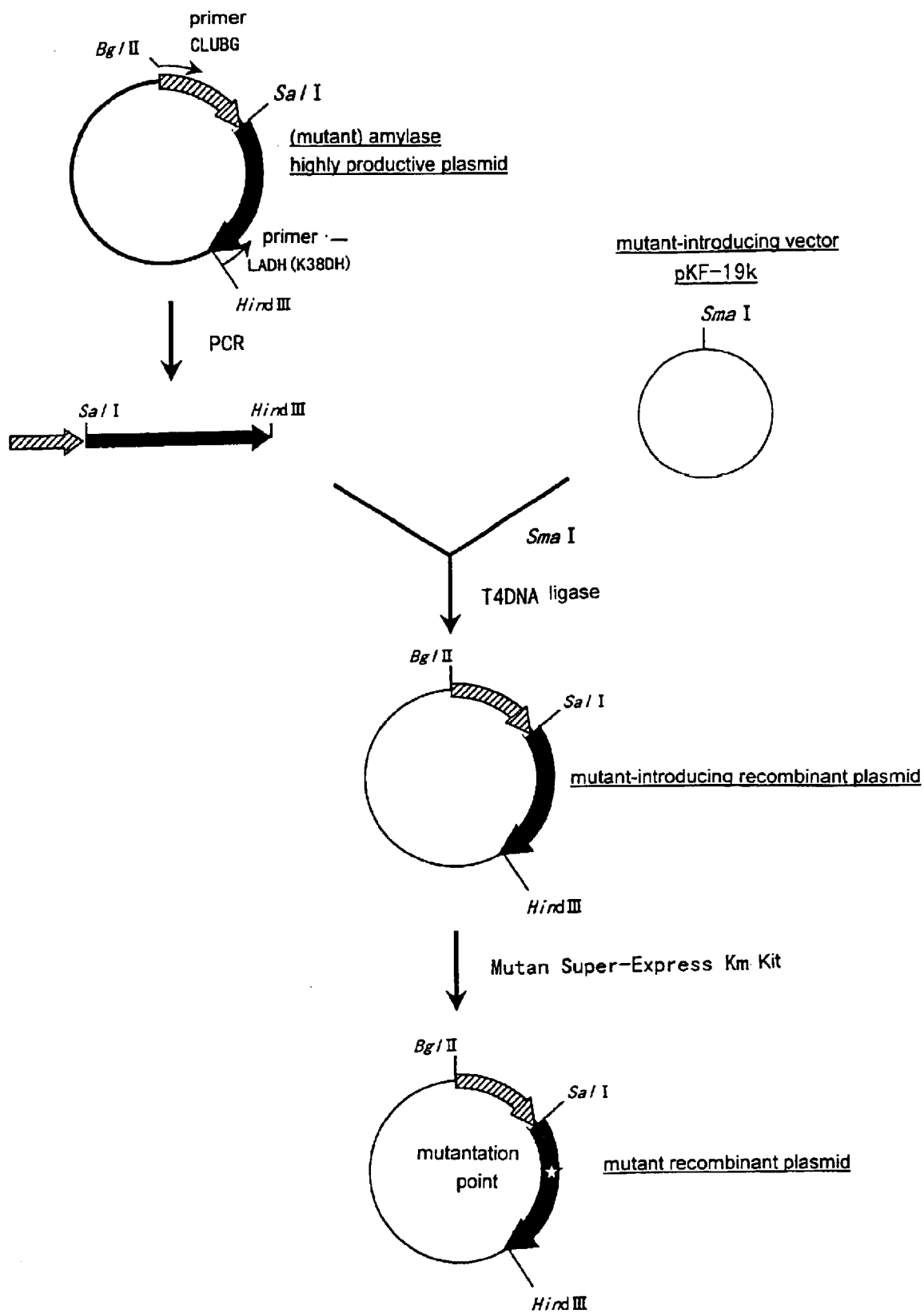
FIG. 2 is a schematic view illustrating a method of introducing a mutation into an α-amylase gene derived from the strain KSM-1378 or KSM-K38.

By using a "Site-Directed Mutagenesis System Mutan-Super Express Km" kit (product of Takara Shuzo Co., Ltd.), the below-described mutations were introduced to the K38AMY and LA-K38AMY. First, the K38AMY and LA-K38AMY gene fragments (about 2.1 kb) were inserted into the site SmaI of a plasmid vector pKF19k attached to the kit to construct a mutagenic recombinant plasmid (FIG. 2). A site-directed mutagenic oligonucleotide primer N190F (SEQ ID No. 50) shown in Table 2 was 5'-phosphorylated with T4 DNA kinase. Using this and the above-described mutagenic recombinant plasmid, mutagenesis was effected in accordance with the method of the kit and by using the reaction product, the strain *Escherichia coli* MV1184 ("Competent cell MV1184", product of Takara Shuzo Co., Ltd.) was transformed. From the transformant thus obtained, a recombinant plasmid was extracted, followed by analysis of a basic sequence, whereby mutation by substitution of Phe for $Asn_{190}$ was confirmed. By repeated introduction of mutagenic reactions into the mutated gene by successively using primers A209V (SEQ ID No. 51) and QEYK (SEQ ID No. 49) in a similar manner as above, thereby substituting $Asn_{190}$ and $Gln_{209}$, each of the amino acid sequence of the K38AMY represented by SEQ ID No. 4 with Phe and Val, respectively, and the sequence from $Asp_1$ to $Gly_{19}$ of the amino acid sequence of the K38AMY represented by SEQ ID No. 4 with the sequence from $His_1$ to $Gly_{21}$ of the amino acid sequence of the LAMY represented by SEQ ID No. 2; by substituting $Gln_{167}$, $Tyr_{169}$, $Asn_{190}$ and $Gln_{209}$, each of the amino acid sequence of the K38AMY, with Glu, Lys, Phe and Val, respectively and the sequence from $Asp_1$ to $Gly_{19}$ of the amino acid sequence of the K38AMY with the sequence from $His_1$ to $Gly_2$, of the amino acid sequence of the LAMY; and substituting $Gln_{167}$ and $Tyr_{169}$, $Asn_{190}$ and $Gln_{209}$, each of the amino acid sequence of the K38AMY, with Glu, Lys, Phe and Val, respectively, genes encoding a mutant α-amylase (which will hereinafter be described as "LA-K38AMY/NFQV") having improved heat resistance, a mutant α-amylase ("LA-K38AMY/QEYKINFQV") having drastically improved heat resistance, and a mutant α-amylase ("QEYK/NFQV") having improved heat resistance were constructed, respectively.

With these genes as a template, PCR reaction was conducted using primers K38US (SEQ ID No. 7) and K38DH (SEQ ID No. 8) to amplify structural gene fragments (about 1.5 kb) encoding the mutant α-amylases were amplified. They were then inserted into the SalI-SmaI site of an expression vector pHSP64 in a similar manner as above, whereby a recombinant plasmid having structural genes of these mutant α-amylases bonded each other was constructed (FIG. 1).

Example 2

Introduction of a Mutation for Improving α-Amylase Productivity

A "Site-Directed Mutagenesis System Mutan-Super Express Km" kit of Takara Shuzo Co., Ltd. was used for site-directed mutagenesis for improving amylase productivity of recombinant Bacillus subtilis. With various recombinant plasmids obtained in Example 1 as a template, PCR reactions were effected using primers CLUBG (SEQ ID No. 9) and LADH (SEQ ID No. 6) for ARG and ΔRG/M202T, while using primers CLUBG (SEQ ID No. 9) and K38DH (SEQ ID No. 8) for K38AMY, LA-K38AMY/NFQV, LA-K38AMY/QEYK/NFQV and QEYK/NFQV, whereby fragments of about 2.1 kb from the upstream strong promoter derived from the strain KSM-64 to the downstream α-amylase gene were amplified. These amplified fragments were inserted into the SmaI site of a plasmid vector pKF19k attached to the above-described kit, whereby various mutagenetic recombinant plasmids were constructed (FIG. 2).

Various oligonucleotide primers for site-directed mutagenesis shown in Table 2 (SEQ ID Nos. 12 to 51) were 5'-phosphorylated with T4DNA kinase, and by using the resultant products and the above mutagenetic recombinant plasmids, mutagenesis was conducted in accordance with the method as described in the kit. With the reaction products, the strain *Escherichia coli* MV1184("Competent Cell MV1184" product of Takara Shuzo Co., Ltd.) was transformed. From the resulting transformants, a recombinant plasmid was extracted, followed by analysis of a base sequence to confirm mutation.

TABLE 2

| SeQ ID No. | Primer | Base sequence (5'-3') | Using purpose |
|---|---|---|---|
| 5 | LAUS | GAGTCGACCAGCACAAGCCCATCATAATGG | PCR for recombination |
| 6 | LADH | TAAAGCTTCAATTTATATTGG | |
| 7 | K38US | GGGTCGACCAGCACAAGCCGATGGATTGAACGGTACGATG | |
| 8 | K38DH | TAAAGCTTTTGTTATTGGTTCACGTACAC | |
| 9 | CLUBG | CCAGATCTACTTACCATTTTAGAGTCA | |
| 10 | LA-K38 | ATTTGCCAAATGACGGGCAGCATTGGAATCGGTT | |
| 11 | LA-K38R | AACCGATTCCAATGCTGCCCGTCATTTGGCAAAT | |
| 12 | P18S | TTTGAATGGCATTTGTCAAATGACGGGGAACCAC | Site-directed mutagenesis (ΔRG) |
| 13 | Q86E | ACAAGGAGTCAGTTGGAAGGTGCCGTGACATCT | |
| 14 | E130V | CGAAACCAAGTAATATCAGGT | |
| 15 | N154D | AATACCCATTCCGATTTTAAATGGCGC | |
| 16 | R171C | GATTGGGATCAGTCATGYCAGCTTCAGAACAAA | |
| 17 | A186V | AAATTCACCGGAAAGGTATGGGACTGGGAAGTA | |
| 18 | E212D | TCATCCAGATGTAATCAATG | |
| 19 | V222E | CTTAGAAAATTGGGGAGAATGGTATACAAATACA | |
| 20 | Y243C | GTGAAACATATTAAATGCAGCTATACGAGAGAT | |
| 21 | P260E | AACACCACAGGTAAAGAAATGTTTGCAGTTGCA | |
| 22 | K269Q | AGAATTTTGGCAAAATGACCT | |
| 23 | E276H | TTGCTGCAATCCATAACTATTTAAAT | |
| 24 | N277S | CTTGCTGCAATCGAAAGYTATTTAAATAAAACA | |
| 25 | R310A | GGCTATTTTGATATGGCAAATATTTTAAATGGT | |
| 26 | E360Q | TCTGACAAGGCAGCAAGGTTA | |
| 27 | Q391E | GATCCACTTCTGGAAGCACGTCAAACG | |
| 28 | W439R | GGGGGTAATAAAAGAATGTATGTCGGG | |
| 29 | K444R | ATGTATGTCGGGCGACATAAAGCTGG | |
| 30 | N471D | GATGGTTGGGGGGATTTCACTGTAA | |
| 31 | G476D | TTCACTGTAAACGATGGGGCAGTTTCG | |
| 32 | K484Q | GGTTTGGGTGCAGCAATAAAT | |
| 33 | P18X | TTTGAATGGCATTTGNNNAATGACGGGGAACCAC | Site-directed mutagenesis (for ΔRG/ M2027) |
| 34 | A186X | AAATTCACCGGAAAGNNNTGGGACTGGGAAGTA | |
| 35 | Y243X | GTGAAACATATTAAANNNAGCTATACGAGAGAT | |
| 36 | N277X | CTTGCTGCAATCGAANNNTATTTAAATAAAACA | |
| 37 | N471E | GATGGTTGGGGGGAATTCACTGTAA | |
| 38 | D128V | CCAACGAATCGTTGGCAGGTAATTTCAGGTGCCTACACG | Site-directed mutagenesis for K38AMY) |
| 39 | G140S | ATTGATGCGTGGACGAGTTTCGACTTTTCAGGG | |
| 40 | S144P | TTTCGACTTTCCAGGGCGTAA | |
| 41 | R168Q | GGTGTTGACTGGGATCAGCAATATCAAGAAAATCATATTTTCC | |
| 42 | N181V | CATATTTTCCGCTTTGCAAATACGGTNTGGAACAGGCGAGTG | |

TABLE 2-continued

| SeQ ID No. | Primer | Base sequence (5'-3') | Using purpose |
|---|---|---|---|
| 43 | E207D | AATATCGACTTTAGTCATCCAGATGTACAAGATGAGTTGAAGGA | |
| 44 | F272S | GACGTAGGTGCTCTCGAATCTTATTTAGATGAAATGAATTGGG | |
| 45 | S375P | CGATAACATTCCAGCTAAAAA | |
| 46 | W434R | GACCTGGTGGTTCCAAGAGAATGTATGTAGGACGTCAG | |
| 47 | E466D | AATGGCGATGGATGGGGCGATTTCTTTACGAATGGAGGATCT | |
| 48 | D128X | CCAACGAATCGTTGGCAGNNNATTTCAGGTGCCTACACG | |
| 49 | QEYK | GTTGACTGGGATGAGCGCAAACAAGAAAATCAT | |
| 50 | N190F | TGGATGAAGAGTTCGGTAATTATGA | |
| 51 | Q209 | AGTCATCCAGAGGTCGTAGATGAGTTGAAGGAT | |

The "N" in the base sequence means a mixed base of A, T, G and C, while "Y" means a mixed base of T and C.

By inserting an expression promoter region and the mutant α-amylase gene portion into the SmaI site of pKF19k again in a similar manner as the above, the mutation-introduced gene became a template plasmid upon introduction of another mutation. Another mutation was thus introduced in a similar manner to the above-described method.

With these mutated recombinant plasmids thus obtained as a template, PCR reaction was conducted using primers CLUBG (SEQ ID No. 9) and LADH (SEQ ID No. 6) or primers CLUBS (SEQ ID No. 9) and K38DH (SEQ ID No. 8) to amplify the mutated gene fragments. After they were cut with SalI, they were inserted into the site of SalI-SmaI site of an expression vector pHSP64, whereby various plasmids for producing mutant α-amylases were constructed (FIG. 1).

Example 3
Production of Mutant α-Amylases

The various plasmids for producing mutant α-amylases obtained in Example 2 were each introduced into the strain Bacillus subtilis ISW1214 (leuA metB5 hsdM1) in accordance with the protoplast method. The recombinant Bacillus subtilis thus obtained was cultivated at 30° C. for 4 days in a liquid medium (corn steep liquor, 4%; tryptose, 1%; meet extract, 1%, monopotassium phosphate, 0.1%, magnesium sulfate, 0.01%, maltose, 2%, calcium chloride, 0.1%, tetracycline, 15 μg/mL). The activity of each of the various mutant α-amylases was measured using the supernatant of the culture medium.

Example 4
Evaluation of Amylase Productivity-1

Each of an enzyme having $Pro_{18}$ of ΔRG substituted with Ser (which will hereinafter be abbreviated as "P18S/ΔRG"), an enzyme having $Gln_{86}$ substituted with Glu ("Q86E/ΔRG"), an enzyme having $Glu_{130}$ substituted with Val ("E130V/ΔRG"), an enzyme having $Asn_{154}$ substituted with Asp ("N154D/ΔRG"), an enzyme having $Arg_{171}$ substituted with Cys ("R171C/ΔRG"), an enzyme having $Ala_{186}$ substituted with Val ("A186V/ΔRG"), an enzyme having $Glu_{212}$ substituted with Asp ("E212D/ΔRG"), an enzyme having $Val_{222}$ substituted with Glu ("V222E/ΔRG"), an enzyme having $Tyr_{243}$ substituted with Cys ("Y243C/ΔRG"), an enzyme having $Pro_{260}$ substituted with Glu ("P260E/ΔRG"), an enzyme having $Lys_{269}$ substituted with Gln ("K269E/ΔRG"), an enzyme having $Glu_{276}$ substituted with His ("E276H/ΔRG"), an enzyme having $Asn_{277}$ substituted with Ser ("N277S/ΔRG"), an enzyme having $Arg_{310}$ substituted with Ala ("R310A/ΔRG"), an enzyme having $Glu_{360}$ substituted with Gln ("E360Q/ΔRG"), an enzyme having $Gln_{391}$ substituted with Glu ("Q391E/ΔRG"), an enzyme having $Trp_{439}$ substituted with Arg ("W439R/ΔRG"), an enzyme having $Lys_{444}$ substituted with Arg ("K444R/ΔRG"), an enzyme having $Asn_{471}$ substituted with Asp ("N471D/ΔRG"), and an enzyme having $Gly_{476}$ substituted with Asp ("G476D/ΔRG") was assayed for amylase productivity. As a control, ΔRG was employed. A relative value (%) of amylase productivity was determined from the amylase productivity of ΔRG set at 100%. The results are shown in Table 3.

TABLE 3

| Enzyme | Relative amylase productivity (%) |
|---|---|
| ΔRG | 100 |
| P18S/ΔRG | 277 |
| Q86E/ΔRG | 119 |
| E130V/ΔRG | 362 |
| N154D/ΔRG | 146 |
| R171C/ΔRG | 235 |
| A186V/ΔRG | 485 |
| E212D/ΔRG | 327 |
| V222E/ΔRG | 135 |
| Y243C/ΔRG | 350 |
| P260E/ΔRG | 142 |
| K269Q/ΔRG | 142 |
| E276H/ΔRG | 231 |
| N277S/ΔRG | 312 |
| R310A/ΔRG | 208 |
| E360Q/ΔRG | 162 |
| Q391E/ΔRG | 127 |
| W439R/ΔRG | 312 |
| K444R/ΔRG | 112 |
| N471D/ΔRG | 292 |
| G476D/ΔRG | 296 |

Any one of the mutant enzymes exhibited higher amylase productivity than ΔRG, indicating that mutation heightened productivity of α-amylase in recombinant Bacillus subtilis. In particular, the productivity of each of E130V/ΔRG, A186V/ΔRG, E212D/ΔRG, Y243C/ΔRG, N277S/ΔRG and W439R/ΔRG was found to be at least 3 times greater than that of ΔRG and above all, A186V/ΔRG exhibited eminently high productivity of almost 5 times greater than that of ΔRG.

Example 5
Evaluation of Amylase Productivity-2

In a similar manner to the methods described in Examples 1, 2 and 3, each of an enzyme having $Pro_{18}$ of ΔRG/MT substituted with Thr (which will hereinafter be abbreviated as "P18T/ΔRG/MT"), an enzyme having $Gln_{86}$ substituted with Glu ("Q86E/ΔRG/MT"), an enzyme having $Glu_{130}$ substituted with Val ("E130V/ΔRG/MT"), an enzyme having $Ala_{186}$ substituted with Asn ("A186N/ΔRG/MT"), an enzyme having $Tyr_{243}$ substituted with Ser ("Y243S/ΔRG/MT"), an enzyme having $Asn_{277}$ substituted with Phe ("N277F/ΔRG/MT"), and an enzyme having $Asn_{471}$ substituted with Glu ("N471E/ΔRG/MT") was assayed for amylase productivity. As a control, ΔRG/MT was employed. The results are shown in Table 4.

TABLE 4

| Enzyme | Relative amylase productivity (%) |
| --- | --- |
| ΔRG/MT | 100 |
| P18T/ΔRG/MT | 200 |
| Q86E/ΔRG/MT | 144 |
| E130V/ΔRG/MT | 344 |
| A186N/ΔRG/MT | 344 |
| Y243S/ΔRG/MT | 189 |
| N277F/ΔRG/MT | 256 |
| N471E/ΔRG/MT | 211 |

It was recognized that any one of the above-described mutant enzymes exhibited high amylase productivity compared with ΔRG/MT, and in particular, the productivity of each of E130V/ΔRG/MT and A186N/ΔRG/MT was at least 3 times greater than that of ΔRG/MT.

Example 6
Evaluation of Amylase Productivity-3

In accordance with the methods employed in Examples 1, 2 and 3, each of an enzyme having $Asp_{128}$ of K38AMY substituted with Val (which will hereinafter be abbreviated as "D128V"), an enzyme having $Gly_{140}$ substituted with Ser ("G140S"), an enzyme having $Ser_{144}$ substituted with Pro ("S144P"), an enzyme having $Arg_{168}$ substituted with Gln ("R168Q"), an enzyme having $Asn_{181}$ substituted with Val ("N181V"), an enzyme having $Glu_{207}$ substituted with Asp ("E207D"), an enzyme having $Phe_{272}$ substituted with Ser ("F272S"), an enzyme having $Ser_{375}$ substituted with Pro ("S375P"), an enzyme having $Trp_{434}$ substituted with Arg ("W434R"), and an enzyme having $Glu_{466}$ substituted with Asp ("E466D") was assayed for amylase productivity. As a control, K38AMY was employed. The results are shown in Table 5.

TABLE 5

| Enzyme | Relative amylase productivity (%) |
| --- | --- |
| K38AMY | 100 |
| D128V | 325 |
| G140S | 209 |
| S144P | 197 |
| R168Q | 264 |
| N181V | 207 |
| E207D | 109 |

TABLE 5-continued

| Enzyme | Relative amylase productivity (%) |
| --- | --- |
| F272S | 175 |
| S375P | 115 |
| W434R | 124 |
| E466D | 212 |

It was recognized that compared with the wild type K38AMY, any one of the mutant enzymes exhibited high amylase productivity and in particular, D128V exhibited high productivity at least 3 times greater than that of K38AMY.

Example 7
Evaluation of Amylase Productivity-4

A mutant enzyme S144P/N181V (which will hereinafter be abbreviated as "SPNV") having, among the mutants shown in Example 6, S144P and N181V in combination was assayed for amylase productivity in accordance with the method as described in Example 3. As a control, K38AMY, S144P and N181V were employed. The results are shown in Table 6.

TABLE 6

| Enzyme | Relative amylase productivity (%) |
| --- | --- |
| K38AMY | 100 |
| S144P | 197 |
| N181V | 207 |
| SPNV | 257 |

As a result, as shown in Table 6, a further improvement in amylase productivity was brought about by combined use.

Example 8
Evaluation of Amylase Productivity-5

In accordance with the methods as described in Examples 1, 2 and 3, each of an enzyme obtained by substituting $Arg_{168}$ of the gene of a heat-resistance improved enzyme LA-K38AMY/NFQV with Gln (which will hereinafter be abbreviated as "R168Q/LA-K38AMY/NFQV"), an enzyme obtained by substituting $Glu_{466}$ of the above-described gene with Asp ("E466D/LA-K38AMY/NFQV"), and an enzyme having double mutations of Example 6 introduced into the gene ("SPNV/LA-K38AMY/NFQV") was assayed for amylase productivity. As a control, LA-K38AMY/NFQV was employed. The results are shown in Table 7.

TABLE 7

| Enzyme | Relative amylase productivity (%) |
| --- | --- |
| LA-K38AMY/NFQV | 100 |
| R168Q/LA-K38AMY/NFQV | 304 |
| E466D/LA-K38AMY/NFQV | 264 |
| SPNV/LA-K38AMY/NFQV | 154 |

As a result, it was recognized that any one of the mutant enzymes obtained in this Example exhibited high amylase productivity at least about 1.5 times greater than that of LA-K38AMY/NFQV and in particular, R168Q/LA-K38AMY/NFQV exhibited about 3 times greater productivity.

Example 9
Evaluation of Amylase Productivity-6

In accordance with the methods as described in Examples 1, 2 and 3, each of an enzyme obtained by substituting $Asp_{128}$ of the gene of a heat-resistance improved enzyme LA-K38AMY/QEYK/NFQV with Val (which will hereinafter be abbreviated as "D128V/LA-K38AMY/QEYK/NFQV") and an enzyme having double mutations of Example 6 introduced into the gene ("SPNV/LA-K38AMY/QEYK/NFQV") was assayed for amylase productivity. As a control, LA-K38AMY/QEYK/NFQV was employed. The results are shown in Table 8.

TABLE 8

| Enzyme | Relative amylase productivity (%) |
| --- | --- |
| LA-K38AMY/QEYK/NFQV | 100 |
| D128V/LA-K38AMY/QEYK/NFQV | 602 |
| SPNV/LA-K38AMY/QEYK/NFQV | 427 |

As a result, it was recognized that any one of the mutant enzymes obtained in this Example exhibited markedly high amylase productivity compared with LA-K38AMY/QEYK/NFQV and in particular, D128V/LA-K38AMY/QEYK/NFQV exhibited drastic increase (about 6 times) in productivity.

Example 10
Evaluation of Amylase Productivity-7

Into D128V/LA-K38AMY/QEYK/NFQV which was recognized to show a drastic increase in productivity among the mutant enzymes shown in Example 9, a mutation for heightening oxidant resistance by substituting $Met_{107}$ with Leu (this mutation will hereinafter be abbreviated as "M107L") was introduced in accordance with the methods as described in Examples 1 and 2 ("ML/DV/LA-K38AMY/QEYK/NFQV").

Then, the gene of the mutant enzyme ML/DV/LA-K38AMY/QEYK/NFQV was assayed for amylase productivity in accordance with the method of Example 4. As a control, D128V/LA-K38AMY/QEYK/NFQV was employed. The results are shown in Table 9.

TABLE 9

| Enzyme | Relative amylase productivity (%) |
| --- | --- |
| D128V/LA-K38AMY/QEYK/NFQV | 100 |
| M107L/D128V/LA-K38AMY/QEYK/NFQV | 115 |

The relative amylase productivity of the mutant enzyme ML/DV/LA-K38AMY/QEYK/NFQV was 115%, indicating that introduction of M107L mutation for reinforcing oxidant resistance did not adversely affect high productivity of amylase in recombinant *Bacillus subtilis*.

Example 11
Evaluation of Amylase Productivity-8

In accordance with the methods as described in Examples 1, 2 and 3, an enzyme obtained by substituting $AsP_{128}$ of the gene of heat-resistance-improved enzyme QEYK/NFQV with Gln (the resultant enzyme will hereinafter be abbreviated as "D128Q/QEYK/NFQV") was assayed for amylase productivity. As a control, QEYK/NFQV was employed. The results are shown in Table 10.

TABLE 10

| Enzyme | Relative amylase productivity (%) |
| --- | --- |
| QEYK/NFQV | 100 |
| D128Q/QEYK/NFQV | 247 |

It was recognized that the mutant enzyme exhibited productivity of at least 2 times greater than that of QEYK/NFQV.

Example 12
Solubility Assay

After storage of each of the mutant enzyme preparations as shown in Table 11 at 4° C. for 1 week, the precipitate formed by centrifugation (13000 rpm, 10 minutes, 4° C.) was separated. The precipitate was suspended in the same volume, as that before centrifugation, of a Tris-HCl buffer (pH 7.0) containing of 2 mM $CaCl_2$. The resulting suspension was diluted about 500-folds with the same buffer to dissolve the former in the latter and enzymatic activity in the resulting solution was measured. The supernatant was diluted in a similar manner and enzymatic activity in it was also measured. Solubility of each of the mutant enzymes was evaluated by comparing the enzymatic activity in each of the precipitate solution and supernatant with that of the preparation before storage at 4° C. The results are shown collectively in Table 11.

TABLE 11

| | Residual activity (%) after storage at 4° C. | |
| --- | --- | --- |
| Enzyme | Supernatant | Precipitate |
| ΔRG | 55 | 40 |
| ΔRG Gln86 → Glu | 83 | 11 |
| ΔRG Pro260 → Glu | 70 | 18 |
| ΔRG Lys269 → Gln | 74 | 27 |
| ΔRG Asn471 → Asp | 74 | 23 |
| ΔRG Lys484 → Gln | 71 | 24 |

As a result, when an improved α-amylase (ΔRG) having heat resistance improved by deleting $Arg_{181}$ and $Gly_{182}$ was stored at 4° C. for one week, precipitation of the enzyme was recognized and only about half of the activity remained in the supernatant. On the other hand, the mutant enzymes obtained by introducing a further mutation in ΔRG-LAMY showed a high activity residual ratio in the supernatant, indicating an improvement in solubility by mutation. In particular, the enzyme having $Gln_{86}$ substituted with Glu showed the highest enzyme solubility and 80% of the enzyme remained in the supernatant under the conditions of this Example.

Example 13
Detergent Composition for Automatic Dish Washer

A detergent composition for automatic dish washer having the composition as shown in Table 12 was prepared, followed by incorporation therein of various mutant enzymes obtained in the productivity increasing method. As a result, the highly productive mutant enzymes exhibited similar or superior detergency to the control enzyme when they were equal in activity.

TABLE 12

| Composition of detergent | (%) |
|---|---|
| Pluronic L-61 | 2.2 |
| Sodium carbonate | 24.7 |
| Sodium bicarbonate | 24.7 |
| Sodium percarbonate | 10.0 |
| No. 1 sodium silicate | 12.0 |
| Trisodium citrate | 20.0 |
| Polypropylene glycol | 2.2 |
| "Silicone KST-04" (product of Toshiba Silicone) | 0.2 |
| "Sokalan CP-45" (product of BASF) | 4.0 |

Capability of Exploitation Industry

By using the mutant α-amylases according to the present invention, α-amylases are available at a high yield from recombinant microorganisms, making it possible to largely reduce the cost of their industrial production. The mutation for productivity increase in the present invention does not adversely affect biochemical properties of the enzymes so that highly productive liquefying alkaline α-amylases having heat resistance, chelating agent resistance and oxidant resistance and being useful as enzymes for a detergent can be produced.

What is claimed is:

1. A mutant α-amylase which is derived from an α-amylase consisting of an amino acid sequence represented by SEQ ID No. 2 by substitution or deletion of at least one amino acid residue corresponding to any one of $Pro_{18}$, $Gln_{86}$, $Glu_{130}$, $Asn_{154}$, $Arg_{171}$, $Ala_{186}$, $Glu_{212}$, $Val_{222}$, $Tyr_{243}$, $Pro_{260}$, $Lys_{269}$, $Glu_{276}$, $Asn_{277}$, $Arg_{310}$, $Glu_{360}$, $Gln_{391}$, $Trp_{439}$, $Lys_{444}$, $Asn_{471}$, and $Gly_{476}$ of the amino acid sequence.

2. A mutant α-amylase according to claim 1, wherein the substitution or deletion of at least one amino acid residue is substitution of the amino acid residue corresponding to $Pro_{18}$ with Ser or Thr, the amino acid residue corresponding to $Gln_{86}$ with Glu, the amino acid residue corresponding to $Glu_{130}$ with Val or Gln, the amino acid residue corresponding to $Asn_{154}$ with Asp, the amino acid residue corresponding to $Arg_{171}$ with Cys or Gln, the amino acid residue corresponding to $Ala_{186}$ with Val or Asn, the amino acid residue corresponding to $Glu_{212}$ with Asp, the amino acid residue corresponding to $Val_{222}$ with Glu, the amino acid residue corresponding to $Tyr_{243}$ with Cys or Ser, the amino acid residue corresponding to $Pro_{260}$ with Glu, the amino acid residue corresponding to $Lys_{269}$ with Gln, the amino acid residue corresponding to $Glu_{276}$ with His, the amino acid residue corresponding to $Asn_{277}$ with Ser or Phe, the amino acid residue corresponding to $Arg_{310}$ with Ala, the amino acid residue corresponding to $Glu_{360}$ with Gln, the amino acid residue corresponding to $Gln_{391}$ with Glu, the amino acid residue corresponding to $TRp4_{439}$ with Arg, the amino acid residue corresponding to $Lys_{444}$ with Arg, the amino acid residue corresponding to $Asn_{471}$ with Asp or Glu, or the amino acid residue corresponding to $Gly_{476}$ with Asp.

3. The mutant α-amylase according to claim 2, wherein the substitution or deletion of at least one amino acid residue is the amino acid residue corresponding to $Pro_{18}$ with Ser or Thr.

4. The mutant α-amylase according to claim 2, wherein the substitution or deletion of at least one amino acid residue is the amino acid residue corresponding to $Gln_{86}$ with Glu.

5. The mutant α-amylase according to claim 2, wherein the substitution or deletion of at least one amino acid residue is the amino acid residue corresponding to $Glu_{130}$ with Val or Gln.

6. The mutant α-amylase according to claim 2, wherein the substitution or deletion of at least one amino acid residue is the amino acid residue corresponding to $Asn_{154}$ with Asp.

7. The mutant α-amylase according to claim 2, wherein the substitution or deletion of at least one amino acid residue is the amino acid residue corresponding to $Arg_{171}$ with Cys or Gln.

8. The mutant α-amylase according to claim 2, wherein the substitution or deletion of at least one amino acid residue is the amino acid residue corresponding to $Ala_{186}$ with Val or Asn.

9. The mutant α-amylase according to claim 2, wherein the substitution or deletion of at least one amino acid residue is the amino acid residue corresponding to $Glu_{212}$ with Asp.

10. The mutant α-amylase according to claim 2, wherein the substitution or deletion of at least one amino acid residue is the amino acid residue corresponding to $Val_{222}$ with Glu.

11. The mutant α-amylase according to claim 2, wherein the substitution or deletion of at least one amino acid residue is the amino acid residue corresponding to $Tyr_{243}$ with Cys or Ser.

12. The mutant α-amylase according to claim 2, wherein the substitution or deletion of at least one amino acid residue is the amino acid residue corresponding to $Pro_{260}$ with Glu.

13. The mutant α-amylase according to claim 2, wherein the substitution or deletion of at least one amino acid residue is the amino acid residue corresponding to $Lys_{269}$ with Gln.

14. The mutant α-amylase according to claim 2, wherein the substitution or deletion of at least one amino acid residue is the amino acid residue corresponding to $Glu_{276}$ with His.

15. The mutant α-amylase according to claim 2, wherein the substitution or deletion of at least one amino acid residue is the amino acid residue corresponding to $Asn_{277}$ with Ser or Phe.

16. The mutant α-amylase according to claim 2, wherein the substitution or deletion of at least one amino acid residue is the amino acid residue corresponding to $Arg_{310}$ with Ala.

17. The mutant α-amylase according to claim 2, wherein the substitution or deletion of at least one amino acid residue is the amino acid residue corresponding to $Glu_{360}$ with Gln.

18. The mutant α-amylase according to claim 2, wherein the substitution or deletion of at least one amino acid residue is the amino acid residue corresponding to $Gln_{391}$ with Glu.

19. The mutant α-amylase according to claim 2, wherein the substitution or deletion of at least one amino acid residue is the amino acid residue corresponding to $Trp_{439}$ with Arg.

20. The mutant α-amylase according to claim 2, wherein the substitution or deletion of at least one amino acid residue is the amino acid residue corresponding to $Lys_{444}$ with Arg.

21. The mutant α-amylase according to claim 2, wherein the substitution or deletion of at least one amino acid residue is the amino acid residue corresponding to $Asn_{471}$ with Asp or Glu.

22. The mutant α-amylase according to claim 2, wherein the substitution or deletion of at least one amino acid residue is the amino acid residue corresponding to $Gly_{476}$ with Asp.

23. A composition comprising the mutant α-amylase of claim 1 and a carrier.

24. A composition comprising the mutant α-amylase of claim 2 and a carrier.

25. A method of making a detergent, comprising adding the mutant α-amylase of claim 1 to one or more detergent components.

26. A method of making a detergent, comprising adding the mutant α-amylase of claim 2 to one or more detergent components.

* * * * *

UNITED STATES PATENT AND TRADEMARK OFFICE
CERTIFICATE OF CORRECTION

PATENT NO. : 6,743,616 B2
DATED : June 1, 2004
INVENTOR(S) : Hiroyuki Araki et al.

It is certified that error appears in the above-identified patent and that said Letters Patent is hereby corrected as shown below:

<u>Column 47,</u>
Line 50, "$TR_p4_{439}$" should read -- $Trp_{439}$ --

Signed and Sealed this

Sixteenth Day of November, 2004

JON W. DUDAS
*Director of the United States Patent and Trademark Office*